United States Patent
Peszynski et al.

(12) 
(10) Patent No.: US 6,592,520 B1
(45) Date of Patent: Jul. 15, 2003

(54) INTRAVASCULAR ULTRASOUND IMAGING APPARATUS AND METHOD

(75) Inventors: Michael Peszynski, Newburyport, MA (US); Heather Beck, Chelmsford, MA (US); David G. Miller, North Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/919,103

(22) Filed: Jul. 31, 2001

(51) Int. Cl.$^7$ ................................................. A61B 8/00
(52) U.S. Cl. ........................ 600/437; 600/460; 600/461
(58) Field of Search ................................. 600/437, 459, 600/460, 461, 462, 467, 488; 382/6

(56) References Cited

U.S. PATENT DOCUMENTS

| | | | | |
|---|---|---|---|---|
| 5,876,343 A | * | 3/1999 | Teo ............................. | 600/443 |
| 6,019,726 A | * | 2/2000 | Webb ........................... | 600/459 |
| 6,315,732 B1 | * | 11/2001 | Suorsa et al. ................ | 600/466 |

* cited by examiner

Primary Examiner—Francis J. Jaworski
Assistant Examiner—Maulin Patel
(74) Attorney, Agent, or Firm—John Vodopia

(57) ABSTRACT

An ultrasound system and method for intravascular imaging is disclosed. The ultrasound system includes an intravascular catheter with an ultrasound transducer array, a transmit beamformer, a receive beamformer, and an image generator. The intravascular catheter has an elongated body made for insertion into a blood vessel and connected to a catheter handle. The catheter includes a catheter core located inside a steerable guide sheath, both having a proximal part and a distal part. The catheter includes an articulation region connected to a positioning device for positioning the transducer array to have a selected orientation relative to an examined tissue region. For each orientation of the transducer array, the transmit and receive beamformers acquire ultrasound data over an image plane of the examined tissue region. The catheter core is connected to a rotation device constructed and arranged to rotate, or oscillate over an angular range, the transducer array that acquires ultrasound data over a multiplicity of image planes. The image generator is constructed to form a selected tissue image based on the acquired ultrasound data.

31 Claims, 40 Drawing Sheets

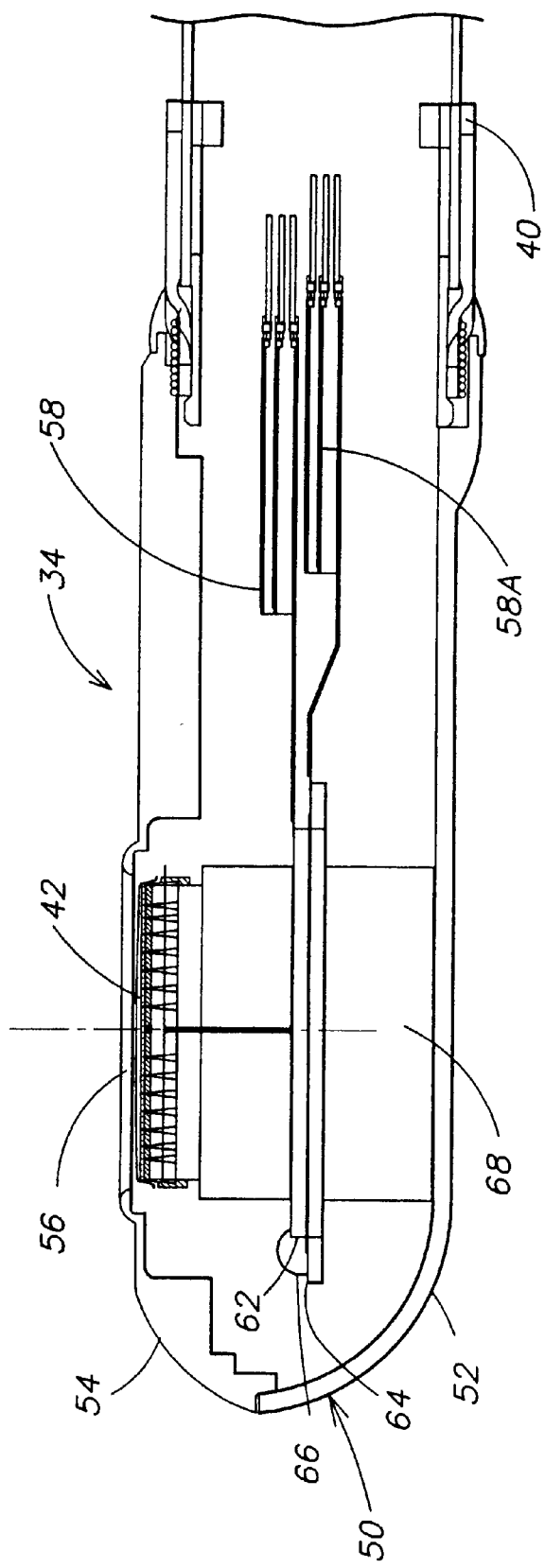

| FIG. 5(1) | FIG. 5(2) | FIG. 5(3) | FIG. 5(4) | FIG. 5(5) |

FIG. 5

| FIG. 5A(1) | FIG. 5A(2) |

FIG. 5A

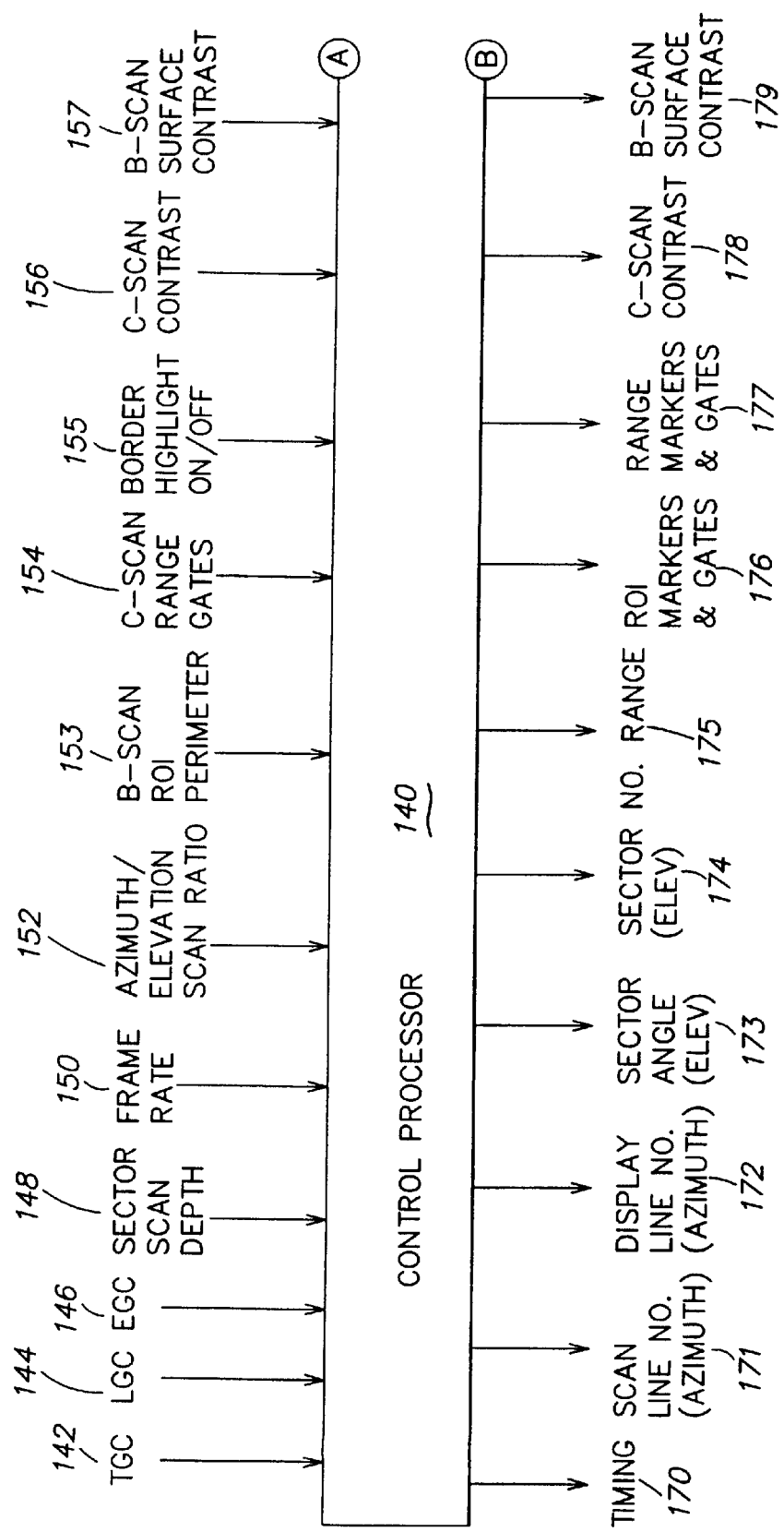
FIG. 5A(1)

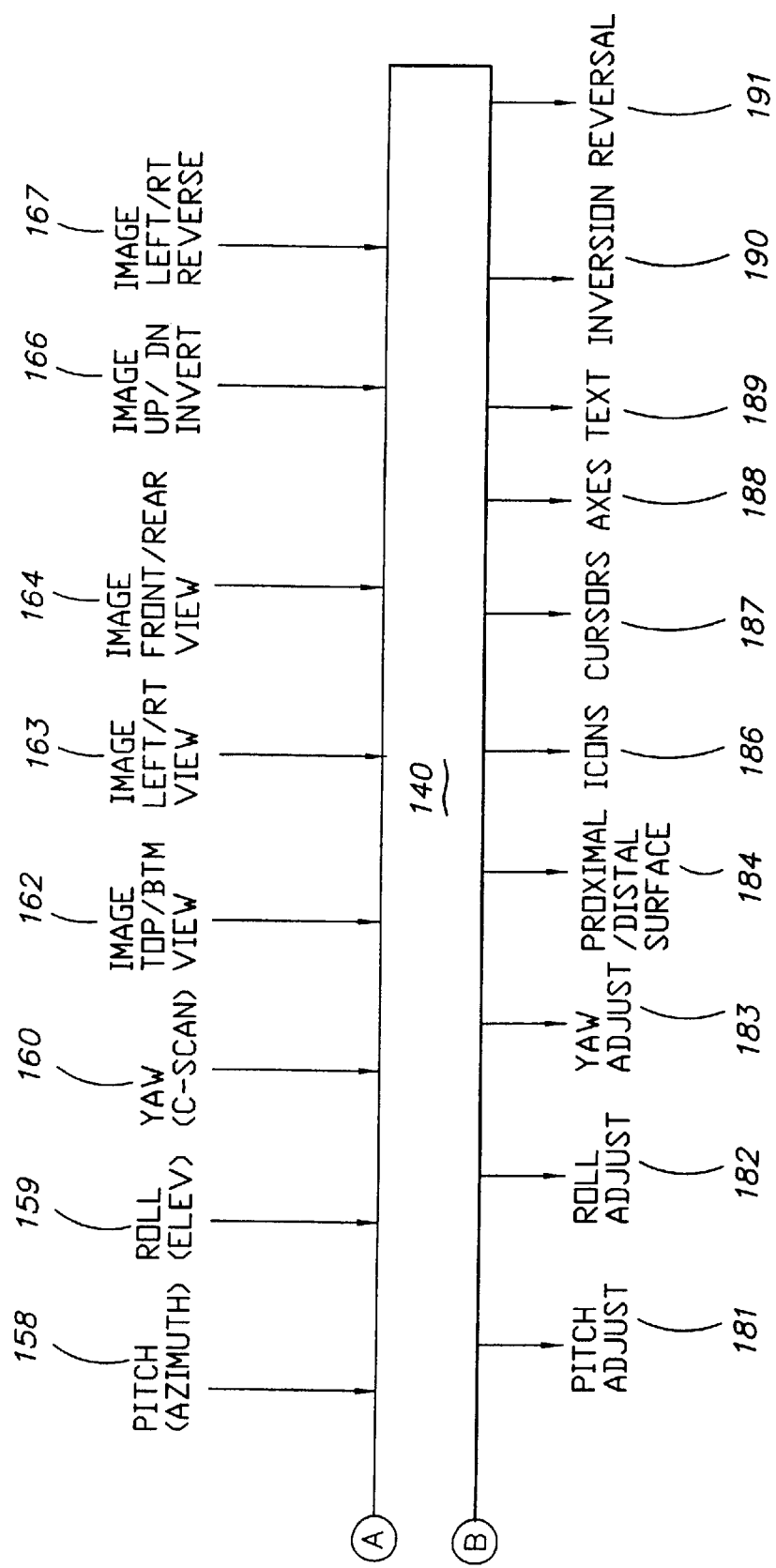
FIG. 5A(2)

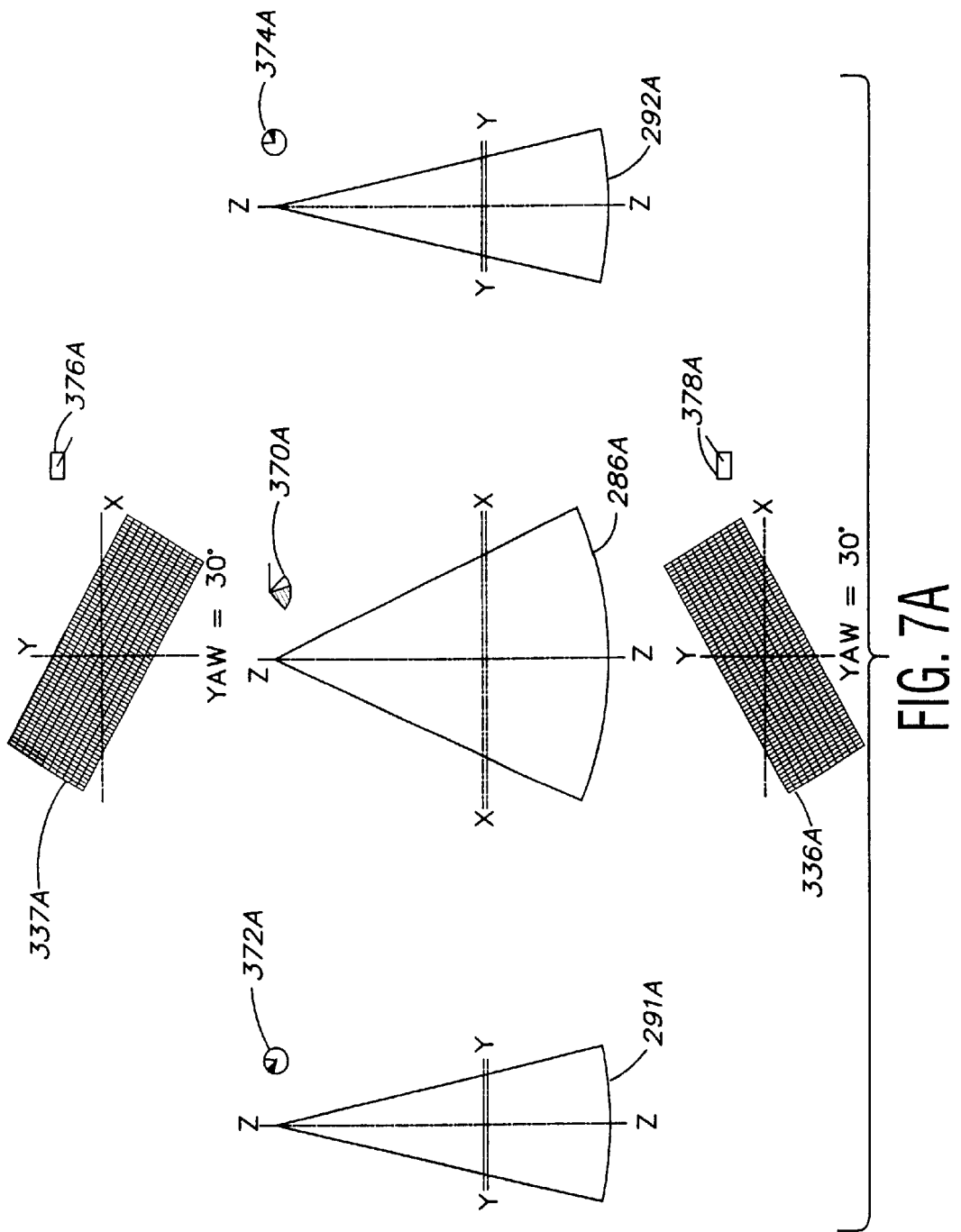

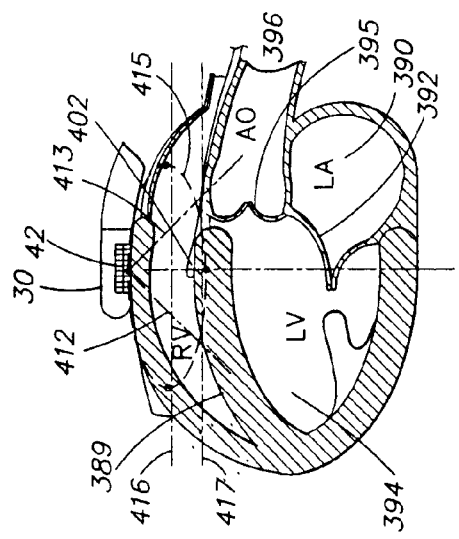
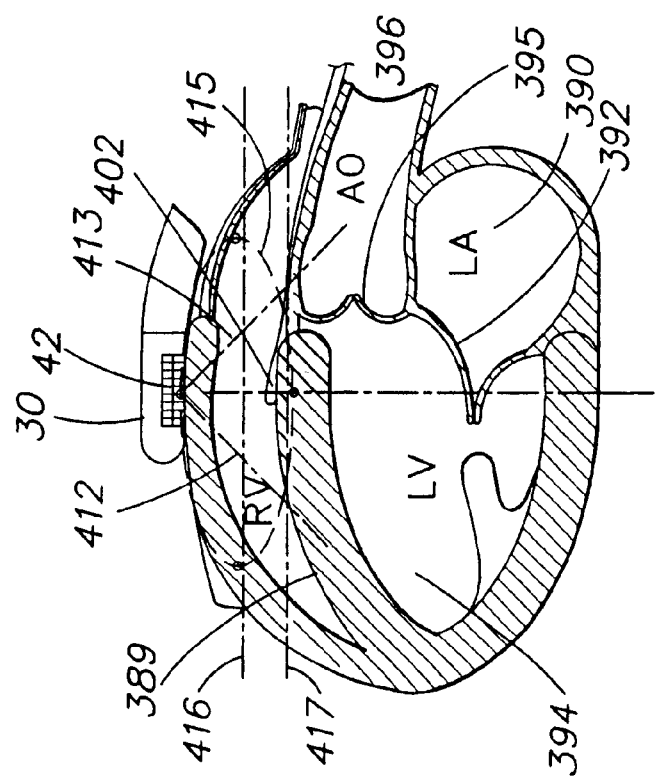
FIG. 9B
FIG. 9A

INTRAVASCULAR ULTRASOUND IMAGING APPARATUS AND METHOD

FIELD OF THE INVENTION

This invention relates to ultrasound devices and methods for imaging internal portions of the human body, and more particularly, to interventional intravascular or intracardiac imaging using catheters with multi-element transducer arrays.

BACKGROUND OF THE INVENTION

Ultrasound imaging has been widely used to observe tissue structures within a human body, such as the heart structures, the abdominal organs, the fetus, and the vascular system. Ultrasound imaging systems include a transducer array connected to multiple channel transmit and receive beamformers applying electrical pulses to the individual transducers in a predetermined timing sequence to generate transmit beams that propagate in predetermined directions from the array. As the transmit beams pass through the body, portions of the acoustic energy are reflected back to the transducer array from tissue structures having different acoustic characteristics. The receive transducers (which may be the transmit transducers operating in the receive mode) convert the reflected pressure pulses into corresponding RF signals that are provided to the receive beamformer. Due to different distances to the individual transducers, the reflected sound waves arrive at the individual transducers at different times, and thus the RF signals have different phases. The receive beamformer has a plurality of processing channels with compensating delay elements connected to a summer. The receive beamformer uses a delay value for each channel and collect echoes reflected from a selected focal point. Consequently, when delayed signals are summed, a strong signal is produced from signals corresponding to this point, but signals arriving from different points, corresponding to different times, have random phase relationships and thus destructively interfere. Furthermore, the beamformer selects the relative delays that control the orientation of the receive beam with respect to the transducer array. Thus, the receive beamformer can dynamically steer the receive beams that have desired orientations and focus them at desired depths. In this way, the ultrasound system acquires echo data.

Invasive, semi-invasive and non-invasive ultrasound systems have been used to image biological tissue of the heart and the vascular system. Doppler ultrasound imaging systems have been used to determine the blood pressure and the blood flow within the heart and the vascular system. The semi-invasive systems include transesophageal imaging systems, and the invasive systems include intravascular imaging systems. A transesophageal system has an insertion tube with an elongated semi-flexible body made for insertion into the esophagus. The insertion tube is about 110 cm long, has about a 30 F diameter and includes an ultrasonic transducer array mounted proximate to the distal end of the tube. The transeophageal system also includes control and imaging electronics including the transmit beamformer and the receive beamformer connected to the transducer array. To image the heart, the transmit beamformer focuses the emitted pulses at relatively large depths, and the receive beamformer detects echoes from structures located 10–20 cm away, which are relatively far in range.

The intravascular imaging systems use an intravascular catheter that requires different design considerations from a transeophageal catheter. The design considerations for an intravascular catheter are unique to the physiology of the vascular system or to the physiology of the heart. The intravascular catheter has an elongated flexible body about 100–130 cm long and about 8F to 14F in diameter. The distal region of the catheter includes an ultrasonic transducer mounted proximate of the distal end. To image the tissue, several mechanical scanning designs have been used. For example, a rotating transducer element or a rotating ultrasound mirror is used to reflect the ultrasound beam in a sweeping arrangement. Furthermore, catheters with several transducer elements have been used, wherein different transducer elements are electronically activated to sweep the acoustic beam in a circular pattern. This system can perform cross-sectional scanning of arteries by sweeping the acoustic beam repeatedly through a series of radial positions within the vessel. For each radial position, the system samples the scattered ultrasound echoes and stores the processed values. However, these ultrasound systems have a fixed focal length of the reflected acoustic beam. The fixed focal length significantly limits the resolution to a fixed radius around the catheter.

Furthermore, intravascular ultrasound imaging has been used for determination of the positions and characteristics of stenotic lesions in the arteries including the coronary arteries. In this procedure, a catheter with a transducer located on the tip is positioned within an artery at a region of interest. As the catheter is withdrawn, the system collects ultrasound data. The imaging system includes a catheter tracking detector for registering the position and the velocity of the transducer tip. The imaging system stacks two-dimensional images acquired for different positions during the transducer withdrawal. An image generator can provide three-dimensional images of the examined region of the blood vessel or the heart, but these images usually have low side penetration.

Recently, ultrasound catheters with the above-described mechanical, rotating transducer designs have increasingly been used in the assessment and therapy of coronary artery diseases. These catheters have a larger aperture, giving rise to deeper penetration depths, which allows imaging of tissue spaced several centimeter away from the transducer, such as the right atrium of the human heart. These images can assist in the placement of electrophysiology catheters. However, these devices still do not provide high quality, real time images of selected tissue regions since they have somewhat limited penetration, a limited lateral control and a limited ability to target a selected tissue region. In general, the produced views are predominantly short axis cross-sectional views with a low side penetration.

Currently, interventional cardiologists rely mainly on the use of fluoroscopic imaging techniques for guidance and placement of devices in the vasculature or the heart as performed in a cardiac catheterization laboratory (Cathlab) or an electrophysiology laboratory (Eplab). A fluoroscope uses X-rays on a real-time frame rate to give the physician a transmission view of the chest cavity, where the heart resides. A bi-plane fluoroscope, which has two transmitter-receiver pairs mounted at 90° to each other, provides real time transmission images of the cardiac anatomy. These images assist the physician in positioning the catheters by providing him (or her) with a sense of the three-dimensional geometry in his (or her) mind that already understands the cardiac anatomy. While fluoroscopy is a useful technique, it does not provide high quality images with real tissue definition. The physician and the assisting medical staff need to cover themselves with a lead suit and need to limit the fluoroscopic imaging time when ever possible to reduce their exposure to X-rays. Furthermore, fluoroscopy may not be available for some patients, for example, pregnant women, due to the harmful effects of the X-rays. The transthoracic and transesophageal ultrasound imaging techniques have been very useful in the clinical and surgical environments, but have not been widely used in the Cathlab or Eplab for patients undergoing interventional techniques.

What is needed, therefore, is an ultrasound system and method for effective intravascular or intracardiac imaging that can visualize three-dimensional anatomy of a selected tissue region. Such system and method would need to use an imaging catheter that enables easy manipulation and positional control. Furthermore, the imaging system and method would need to provide convenient targeting of the selected tissue and good side penetration allowing imaging of near and more distant tissue structures, such as the right and left sides of the heart.

SUMMARY OF THE INVENTION

The present invention is an ultrasound system and method for intravascular imaging. According to one aspect, an ultrasound system for imaging biological tissue includes an intravascular catheter with an ultrasound transducer array, a transmit beamformer, a receive beamformer, and an image generator. The intravascular catheter has an elongated body made for insertion into a blood vessel and connected to a catheter handle. The catheter includes a catheter core located inside a steerable guide sheath, both having a proximal part and a distal part. The catheter includes an articulation region connected to a positioning device for positioning the transducer array to have a selected orientation relative to an examined tissue region. For each orientation of the transducer array, the transmit and receive beamformers acquire ultrasound data over an image plane of the examined tissue region. The catheter core is connected to a rotation device constructed and arranged to rotate, or oscillate over an angular range, the transducer array that acquires ultrasound data over a multiplicity of image planes. The image generator is constructed to form a selected tissue image based on the acquired ultrasound data.

According to another aspect, in an ultrasound system for imaging biological tissue, including an array of ultrasound transducers connected to transmit and receive beamformers constructed to obtain an ultrasound image of a selected tissue region, providing an intravascular catheter. The intravascular catheter includes an imaging core and a steerable guide sheath. The steerable guide sheath includes a distal sheath part and a proximal sheath part constructed for insertion into a blood vessel. The distal sheath part includes an articulation region constructed to assume a selected orientation. The imaging core includes a distal core part, located within the distal sheath part, and a proximal core part, located within the proximal sheath part, and being constructed for rotational motion inside the guide sheath. The ultrasound transducer array is disposed longitudinally on the distal core part of the imaging core. A positioning device is constructed to control the selected orientation of the articulation region and thereby orient the ultrasound transducer array relative to the selected tissue region. The ultrasound transducer array is constructed to detect ultrasound data over an image sector defined by an azimuthal angular range. A rotation device constructed to rotationally displace, over an elevation angular range, the ultrasound transducer array about the apex of the image sector.

According to another aspect, an ultrasound system for imaging biological tissue includes a catheter with a catheter handle, a transmit beamformer, a receive beamformer, and an image generator. The catheter includes core means including an ultrasound transducer array disposed longitudinally on a distal part of the core means, guide sheath means for receiving the core means and enabling defined rotational movement of the core means. The catheter also includes articulation means, connected to positioning means, for orienting the transducer array relative to a tissue region of interest and rotation means, connected to the core means, for oscillating the transducer array over a selected elevation angular range. The transmit beamformer and the receive beamformer are connected to the transducer array and constructed to acquire, for each elevation angle of the transducer array, ultrasound data of an image sector defined by an azimuthal angular range. The image generator is constructed to receive ultrasound data over a multiplicity of image sectors for different elevation angles and to form an image of the tissue region of interest from the ultrasound data.

Preferred embodiments of these aspects include at least one of the following features:

The ultrasound system and the catheter are constructed to collect the ultrasound data over a selected volume defined by an azimuthal angular range and an elevation angular range. The ultrasound system and the catheter are constructed and arranged for real-time imaging capable of achieving a scanning frequency of at least 15 Hz.

The imaging core and the steerable guide sheath are connected to a catheter handle. The catheter handle further includes a rotation device and a compensation mechanism. The compensation mechanism is arranged to counter balance the motion of the rotation device in order to reduce unwanted vibrations in the handle. The accelerometer may provide a signal to the compensation mechanism.

The rotation device includes a drive motor connected to the imaging core and the compensation mechanism includes a counter balance motor. The compensation mechanism is designed to have a natural frequency response at a frequency of oscillation of the ultrasound array.

The rotation device includes a drive motor constructed and arranged to oscillate the imaging core at varying frequencies above a resonance frequency of about 15 Hz.

The rotation device includes a drive motor constructed and arranged to oscillate the ultrasound array over selected angles of the elevation angular range. The rotation device is further constructed and arranged to position the ultrasound array at a selected angle relative to the tissue region of interest and maintain the array at the angle for a selected period of time. The rotation device may include a stepper motor connected to the imaging core.

The intravascular catheter further includes a set of bearings disposed between the imaging core and the guide sheath and arranged to facilitate the rotation or oscillation of the ultrasound array about the apex of the image sector. The bearings may have a low profile and may be molded into the guide sheath. The bearings may have a hydrostatic design.

The catheter handle includes an accelerometer connected to the compensation mechanism and arranged to detect unwanted vibrations in the handle. The accelerometer may provide a signal to the compensation mechanism.

The catheter includes a position sensor constructed and arranged to detect orientation of the ultrasound array and provide a feedback signal to the rotation device. The position sensor may be located in the distal sheath. The position sensor may include an acoustic time-of-flight positioning system with a transmitter and a detector. The position sensor may include an AC electromagnetic tracking sensor or a DC electromagnetic tracking sensor.

The catheter includes an accelerometer sensor arranged to detect vibrations due to the movement of the imaging core.

The articulation region of the catheter includes a multiplicity of articulation links cooperatively arranged with a first articulation mechanism. The first articulation mechanism includes at least one push-pull rod connected to the positioning device. The catheter may further include a sensor constructed and arranged to detect displacement of the push-pull rod. The positioning device may include a rack and pinion mechanism. The articulation links and the push-pull rod are cooperatively arranged to flex in-plane the distal portion upon actuation by the positioning device. The articulation region may form an in-plane J hook.

The catheter further includes a second articulation mechanism. The second articulation mechanism includes a second push-pull rod cooperatively arranged with the articulation links to flex out-of-plane the distal portion (i.e., an out-of-plane J hook) upon actuation by the positioning device.

The catheter includes two push-pull rods and a multiplicity of articulation links included in the articulation region. The multiplicity of links are cooperatively arranged with the push-pull rods to flex in-plane the distal portion to form an S-like curve upon actuation of the push-pull rods by the positioning device. The catheter may further include a third articulation mechanism. The third articulation mechanism includes a third push-pull rod cooperatively arranged with the articulation links to further flex out-of-plane the distal portion (i.e., an out-of-plane S hook) upon actuation by the positioning device.

The imaging core includes a drive shaft constructed to exhibit a high torsional stiffness and a high bending flexibility. The drive shaft may be made of at least two counter wound springs.

The imaging core is removably insertable into the steerable guide sheath. The steerable guide sheath is connectable to a sheath handle, which is connectable to the catheter handle. The sheath handle may further include a v-band clamp constructed and arranged to lock into position the guide sheath relative to the handle. The guide sheath may be disposable or reusable upon cleaning and sterilization. The guide sheath further includes an ultrasonically transparent window located in front of the transducer array.

The catheter further includes a filling port constructed and arranged to provide a coupling medium between the distal sheath part and the distal core part. The filling port may be located near the catheter handle.

The catheter further includes a flush port located in the distal sheath part and arranged in communication with the volume between the distal sheath part and the distal core part.

The position sensor may be constructed and arranged to provide a feedback signal providing the position of the imaging core to the drive motor. The drive motor includes a rotary encoder constructed and arranged to provide an angular position feedback.

The ultrasound system may be constructed and arranged to perform a four dimensional scan of the tissue volume.

According to another aspect, a method for imaging biological tissue includes inserting into a blood vessel an elongated body of an intravascular catheter with an ultrasound transducer array positioned longitudinally on a distal part of the elongated body. The transducer array is connected to a transmit beamformer and a receive beamformer. The method also includes positioning the transducer array to have a selected orientation relative to an examined tissue region, and for each orientation of the transducer array, acquiring ultrasound data over an image plane of the examined tissue region. The method also includes rotating, or oscillating over an angular range, the transducer array and acquiring ultrasound data over a multiplicity of the image planes, and forming a selected tissue image of the tissue region based on the acquired ultrasound data.

Advantageously, the articulation mechanism, located preferably within the catheter sheath, orients the transducer array located preferably on the distal part of the imaging core. The ultrasound system collects echo data over a selectable predictable tissue volume and provides a corresponding data volume. The selectable location and orientation of the data volume improves significantly the tissue images. A clinician may select rotation speed or scanning frequency of the ultrasound array to collect two-dimensional images of selected tissue including a moving organ. The imaging system enables understandable visualization of the tissue providing images with a known orientation. A video display provides anatomically correct orientation of the images.

Furthermore, there are several advantages to positioning the transducer array near the tissue of interest and performing near-in field imaging (as opposed to far-in field imaging performed by the non-invasive or semi-invasive ultrasound system, i.e., transthoracic or transesophageal ultrasound systems). For example, placing the transducer close to the tissue of interest substantially reduces the number of scattering, absorbing, and aberating tissue structures, which degrade acoustic images.

The intravascular catheter has a small diameter that fits through the vascular system used to position the transducer array relatively close to the tissue of interest, for example, the heart tissue. This small diameter dictates a small elevation aperture of the transducer array. The small aperture requires a higher ultrasound frequency to reduce the beam width and thus improve resolution. While higher frequencies are absorbed more rapidly in the tissue, here this is not a problem because the transducer array is positioned relatively close to the tissue of interest. The beam width also varies with the range, but focussing of the beam improves the beam width at the point of focus. A low f-number is required for improved resolution. For an adequate depth of field, acoustic images generally require an f-number of about 2 to 4, which places the area of best resolution (or focus) at two to four times the aperture; this corresponds to the range of 4 mm to 8 mm in the elevation direction.

There are additional benefits of the intravascular imaging. The transducer is always surrounded by blood thereby enabling perfect acoustic coupling to surrounding myocardium or other vessels, organs or tissue being imaged. On the other hand, a poor acoustic contact in transesophageal and transthoracic imaging can create problems ranging from intermittent loss of image to complete inability to acquire an image. This can increase diagnostic time and be devastating to an interventionalist relying on real time echo data to guide intervention devices.

BRIEF DESCRIPTION OF THE DRAWINGS

FIG. 5A shows the distal part of the steerable guide sheath articulated as an out-of-plane J hook.

FIG. 7A shows various imaging volumes generated by the catheter having the distal part articulated in the manner shown in FIGS. 5 through 5B.

DESCRIPTION OF PREFERRED EMBODIMENTS

Figure 1:
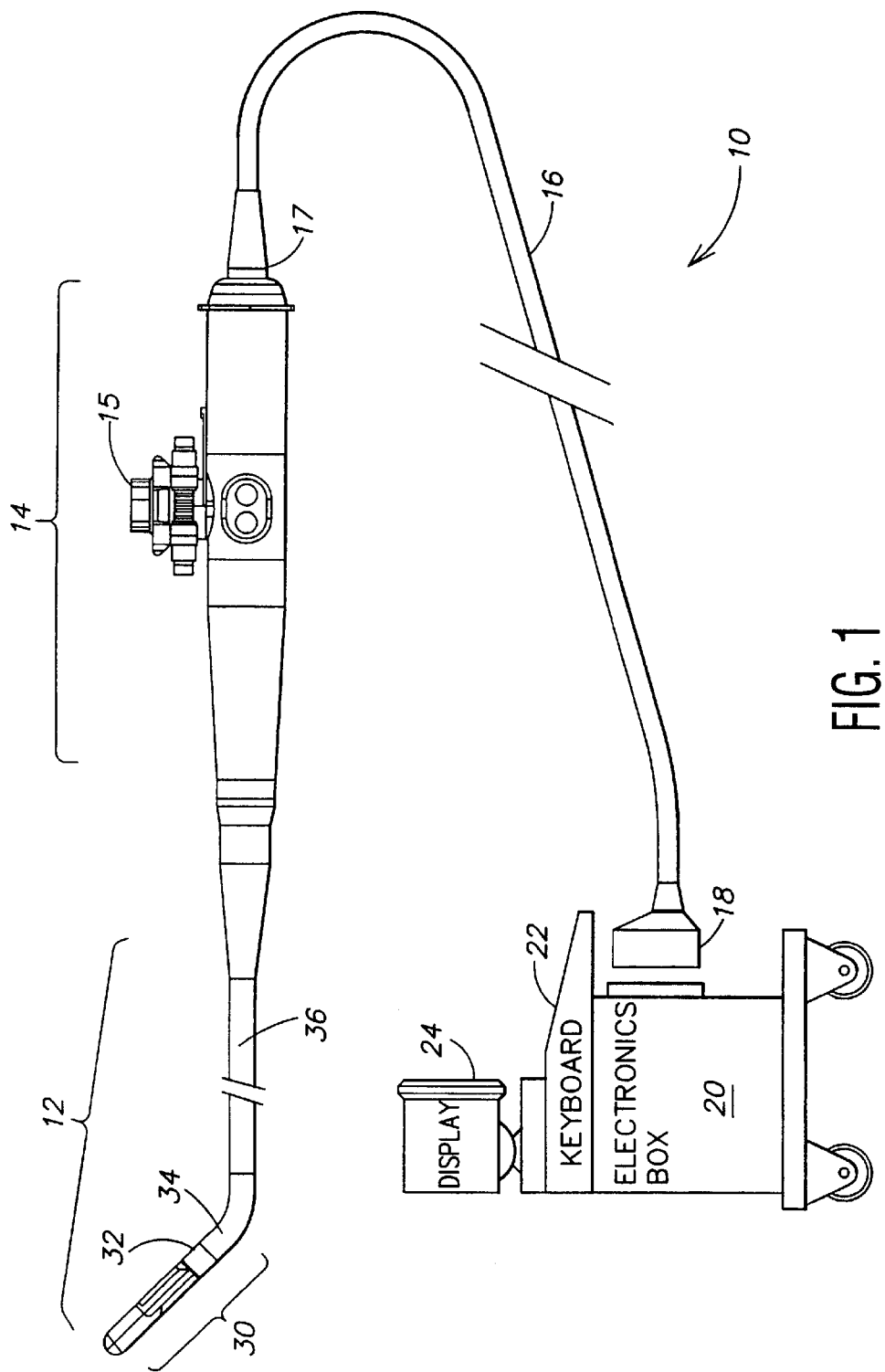
FIG. 1 illustrates an ultrasound system for invasive intravascular imaging of internal tissue.

Referring to FIG. 1, an ultrasonic imaging system 10 includes an imaging catheter 12 with a catheter handle 14 connected by a cable 16, a strain relief 17, and a connector 18 to an electronics box 20. Electronics box 20 is interfaced with a keyboard 22 and provides imaging signals to a display 24. Electronics box 20 includes a transmit beamformer, a receive beamformer, and an image generator. Imaging catheter 12 has a distal part 30 connected to an elongated part 36. The proximal end of elongated part 36 is connected to the distal end of catheter handle 14. Distal part 30 of catheter 12 includes a rigid region 32 and a flexible region 34, which has a length of about one to three times the length of rigid region 32. Flexible region 34 is connected to the distal end of elongated part 36. Elongated part 36 has a low bending stiffness and a high torsional stiffness.

Figure 2A:
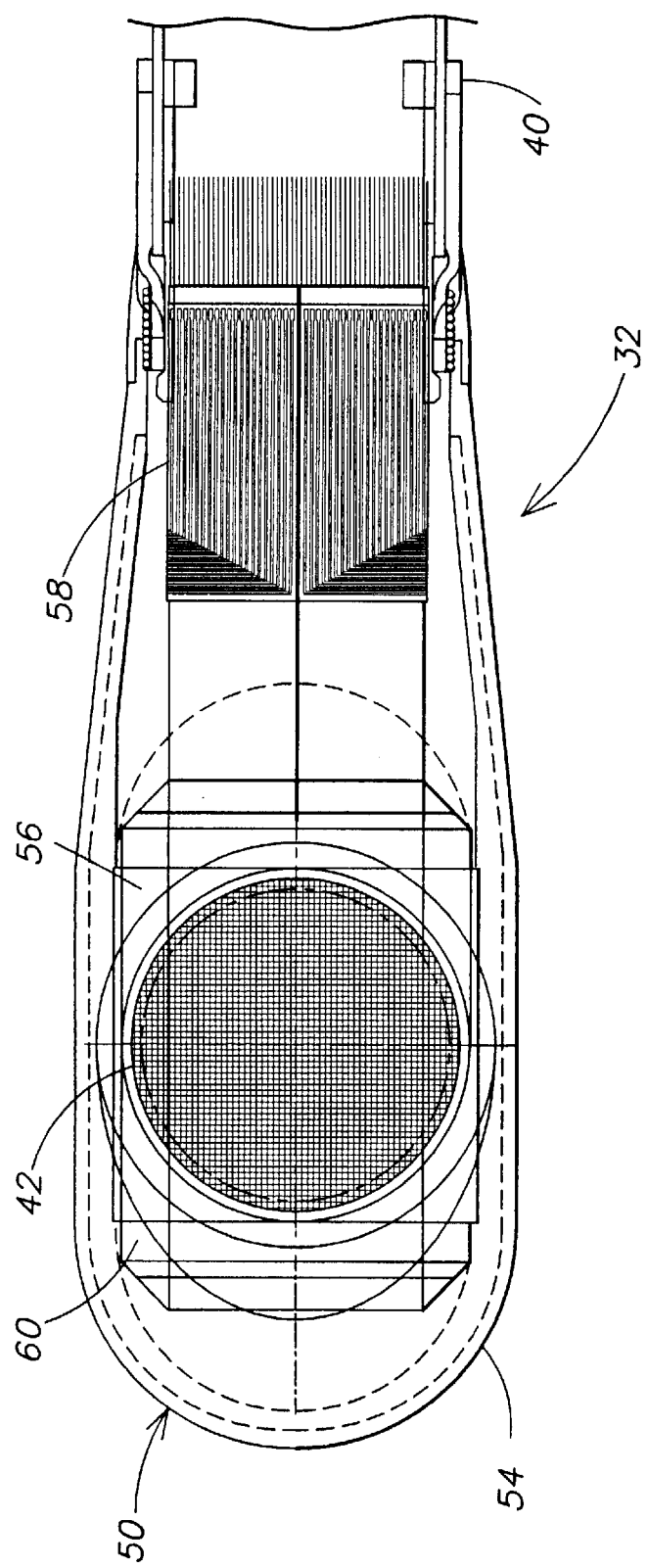
FIG. 2 shows an intravascular imaging catheter including an imaging core insertable into a steerable guide sheath.

Also referring to FIG. 2, imaging catheter 12 includes an imaging core 40 insertable into a steerable guide sheath 60. Steerable guide sheath 60 includes a distal sheath part 30A having a rigid sheath region 32A and an articulation region 34A. Steerable guide sheath 60 is at its proximal end connected to a guide sheath handle 14A. Imaging core 40 includes a distal core part 30B and a flexible, elongated core part 36B. Distal core part 30B includes a rigid core region 32B and a flexible core region 34B. When imaging core 40 is fully inserted into guide sheath 60, rigid core region 32B is located inside rigid sheath region 32A (shown together as rigid region 32 in FIG. 1), flexible core region 34B is located inside articulation region 34A (shown together as flexible region 34 in FIG. 1.), and elongated core part 36B is located inside elongated sheath part 36A (shown together as elongated part 36 in FIG. 1). Guide sheath handle 14A is connectable to handle 14. Guide sheath 60 may be disposable or reusable. The entire catheter 12 has a diameter of about 8 to 14 french and preferably 12 french.

Figure 3:
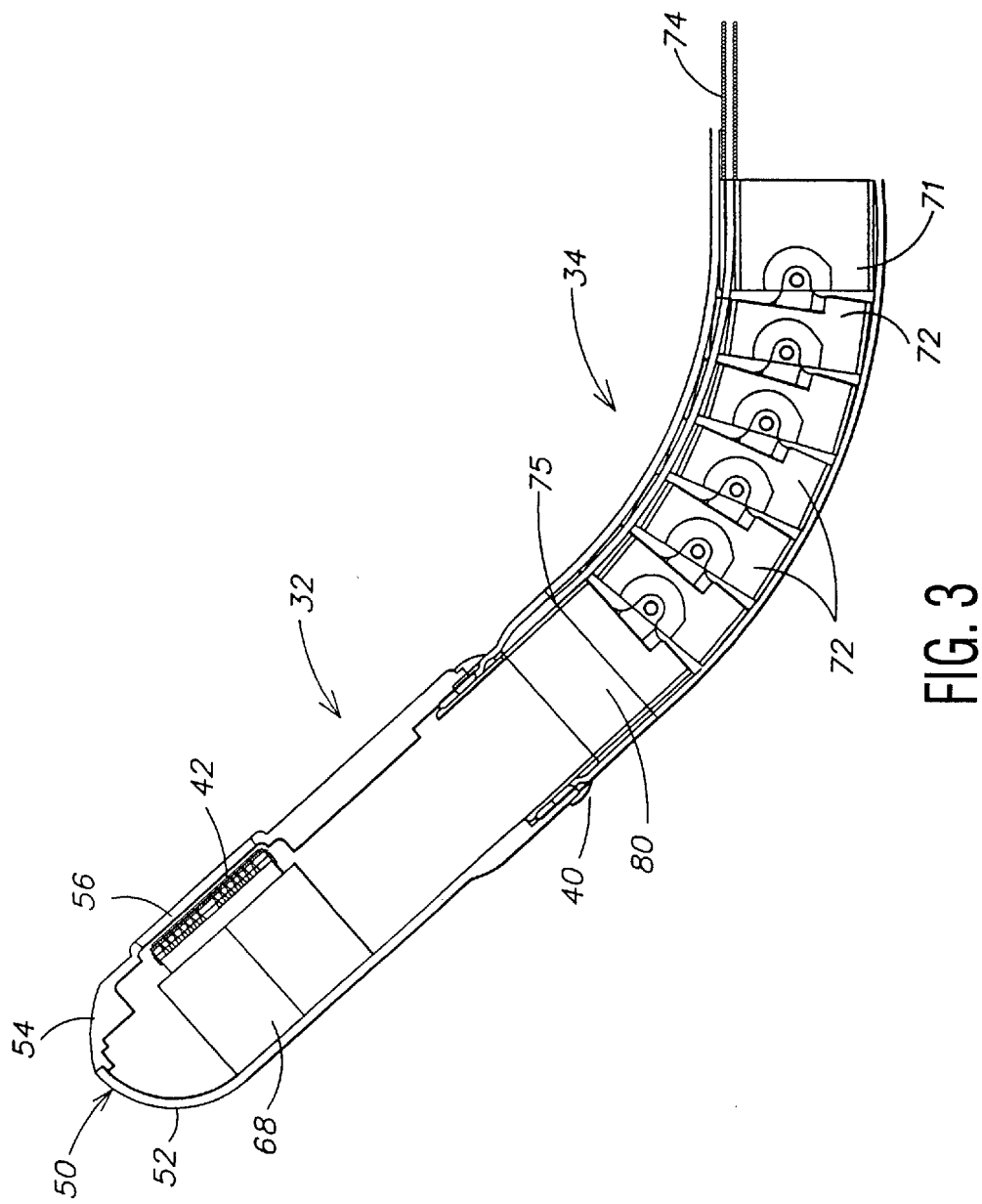
FIGS. 3, 3A, 3B and 3C show a cross-sectional view of the imaging core.
Figure 3A:
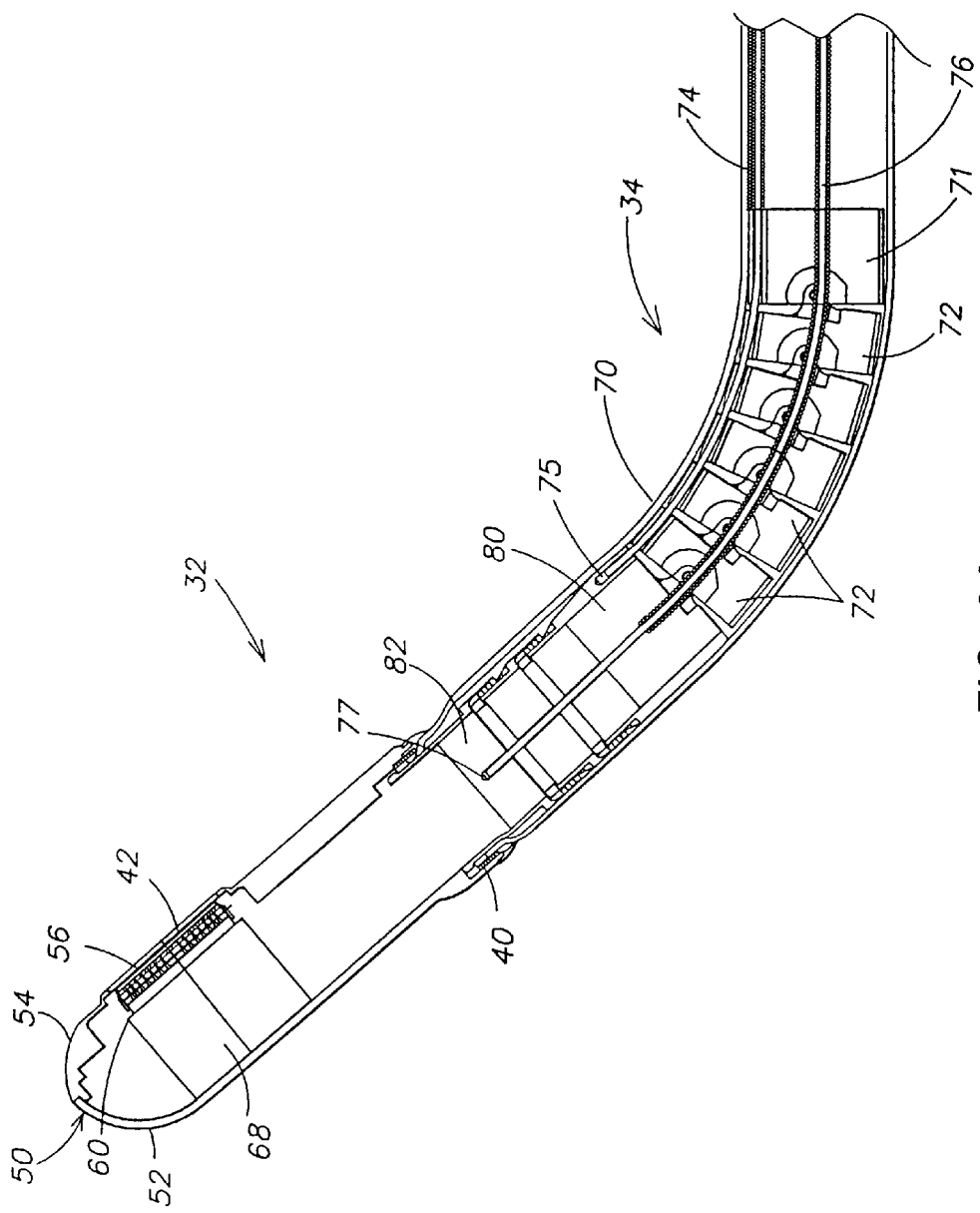
Figure 3B:
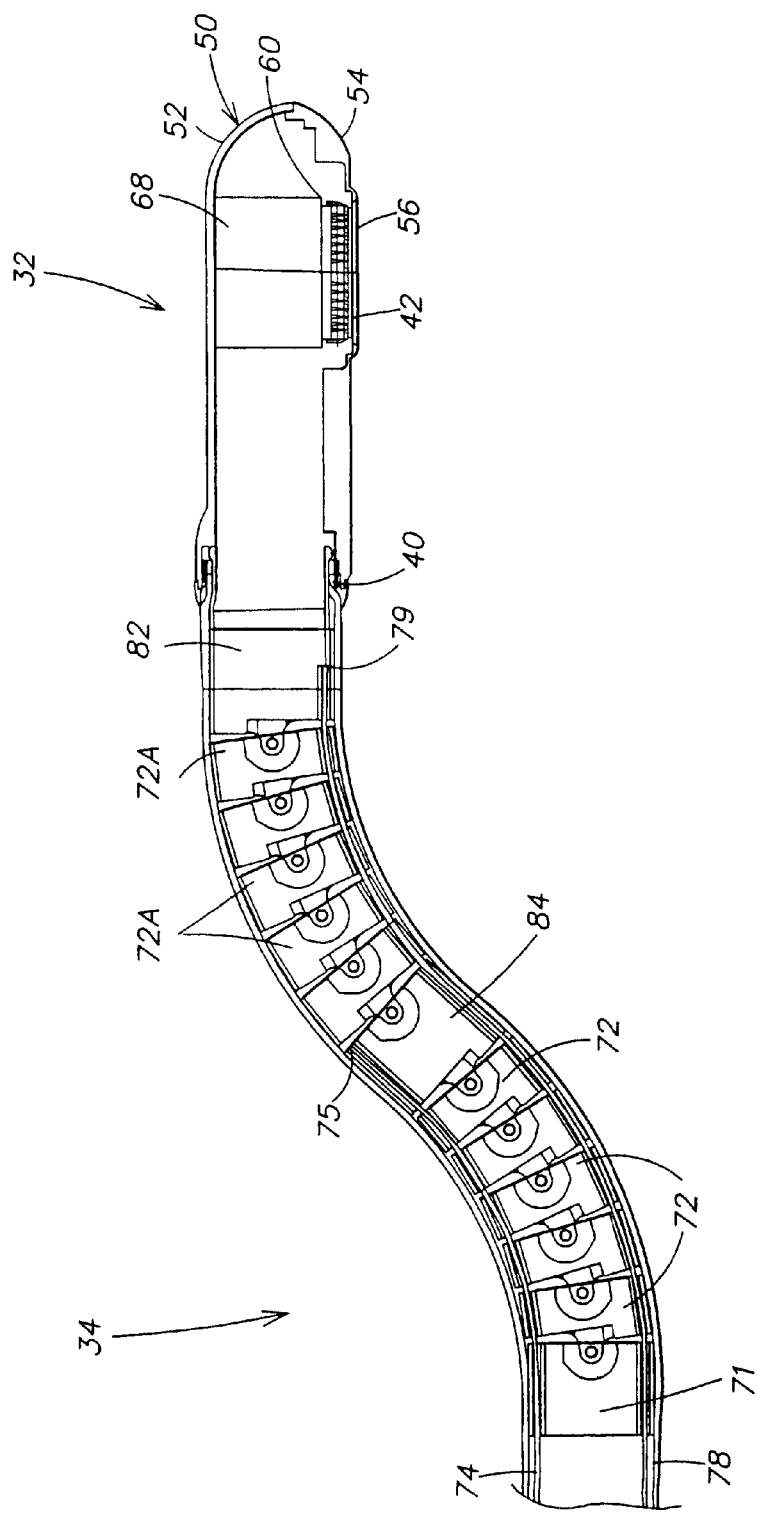
Figure 3C:
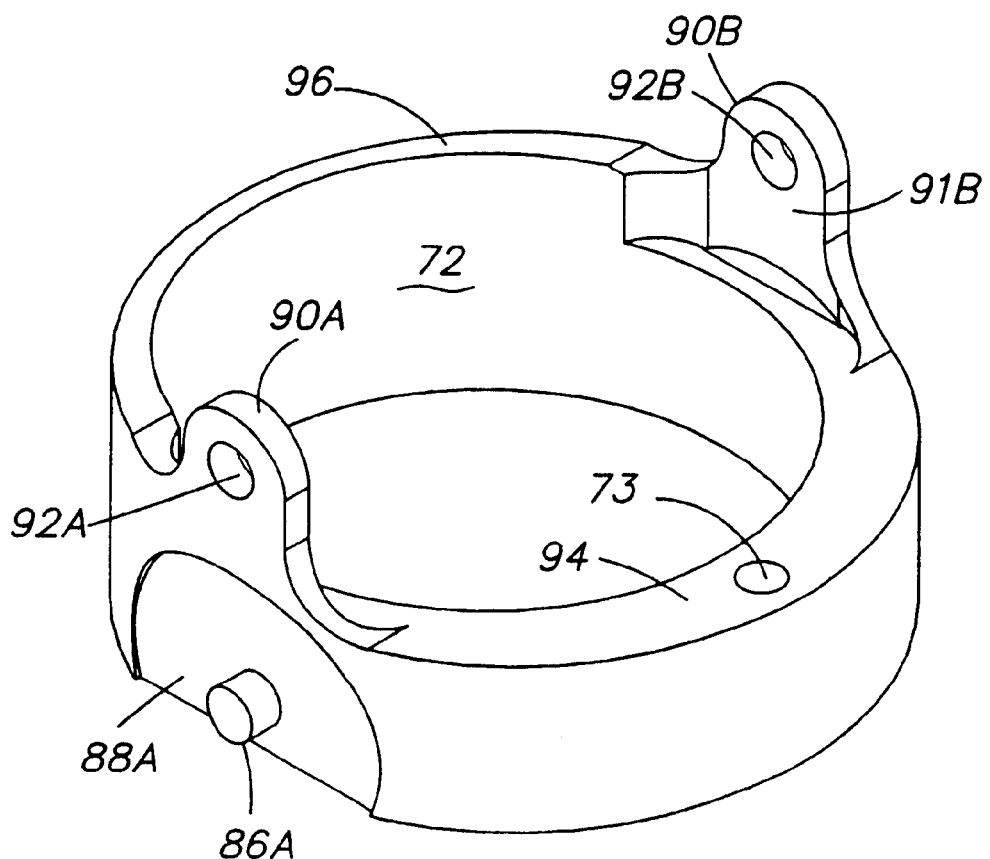
Figure 4:
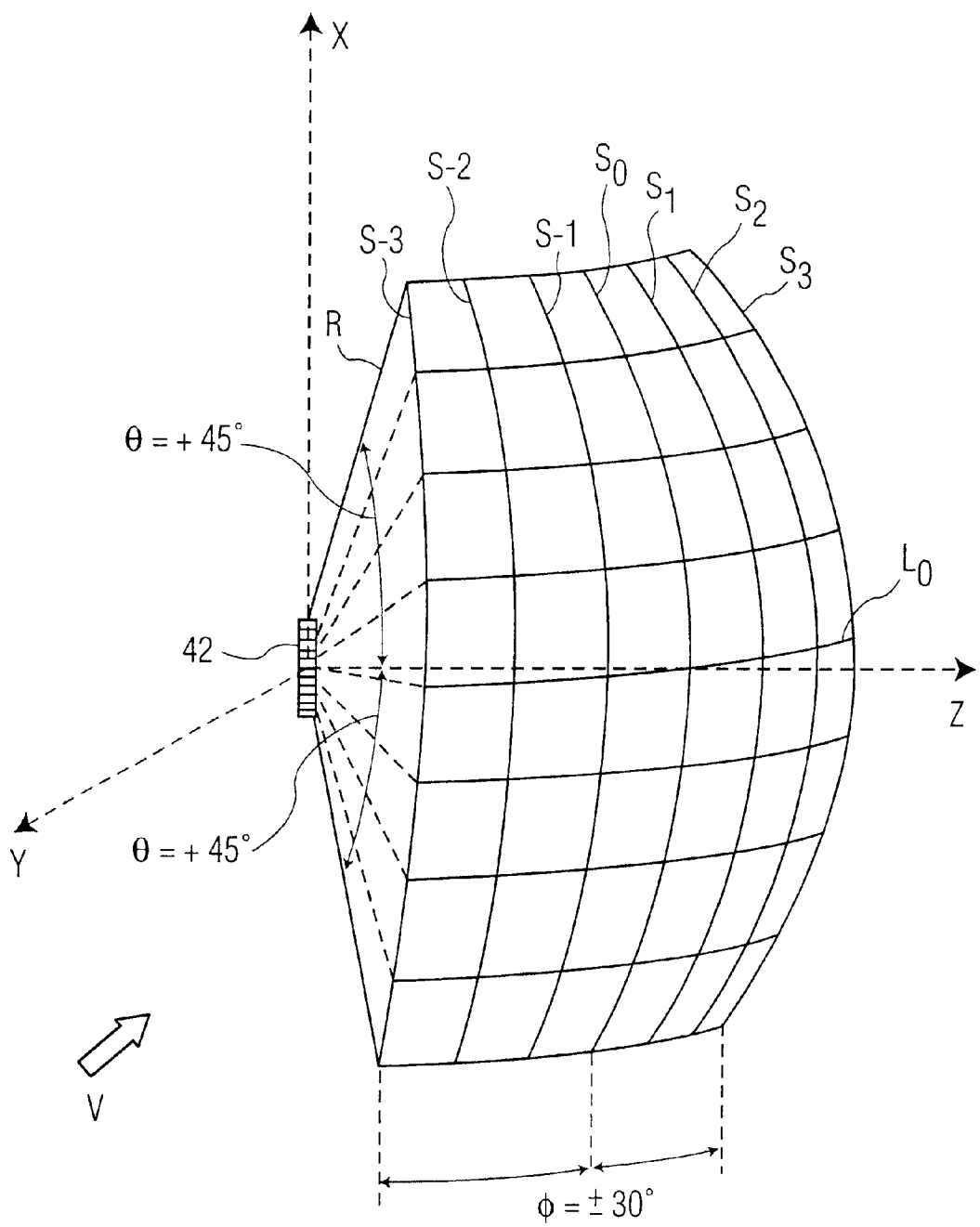
FIGS. 4, 4A, 4B, 4C, 4D and 4E show cross-sectional views of different embodiments of the steerable guide sheath shown in FIG. 2.
Figure 4A:
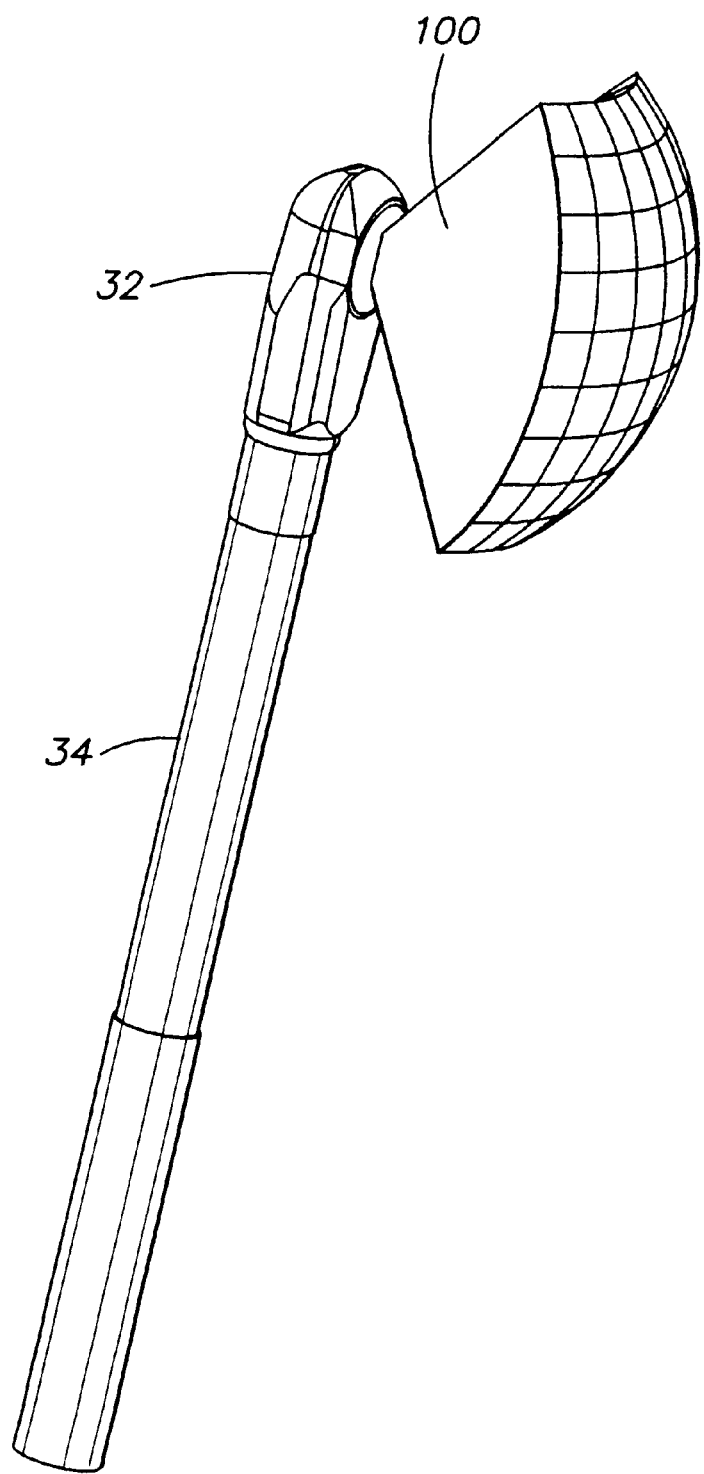
Figure 4B:
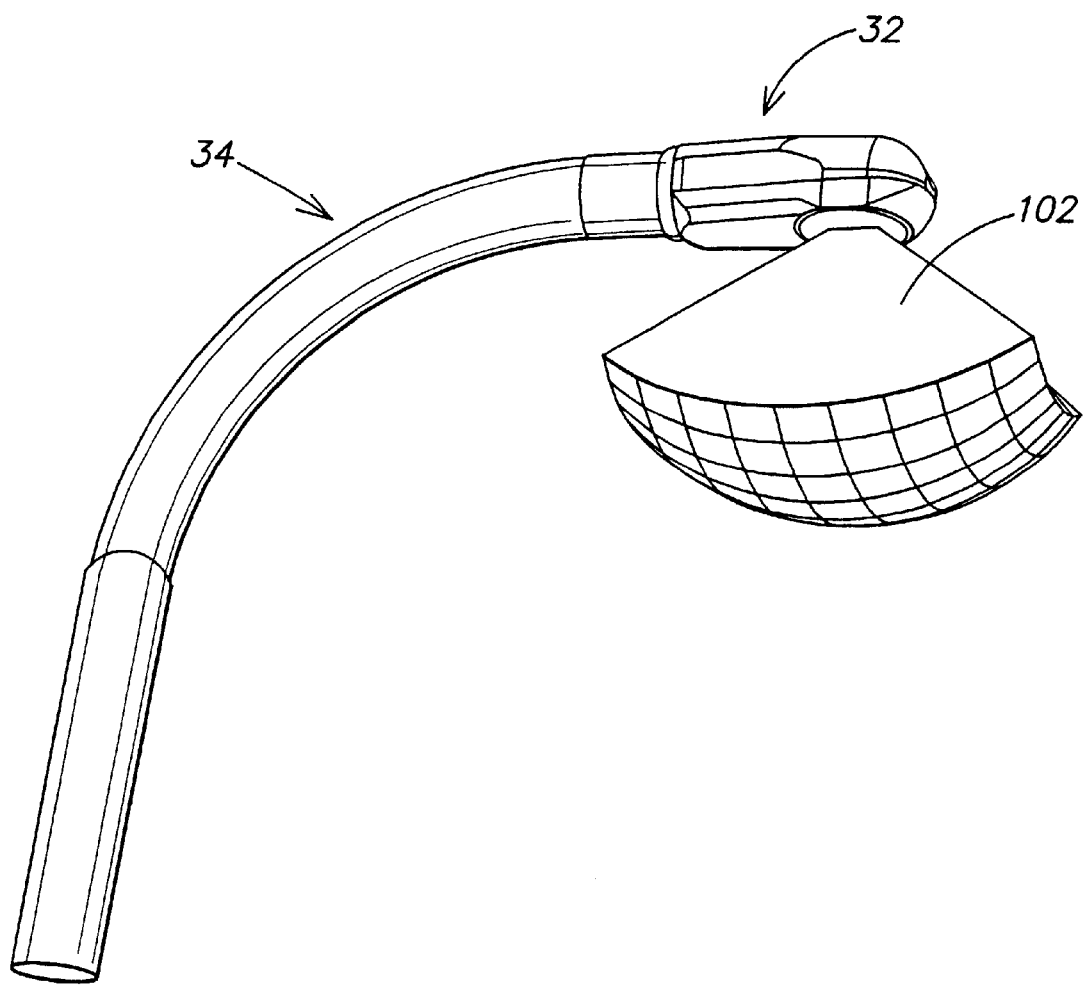
Figure 4C:
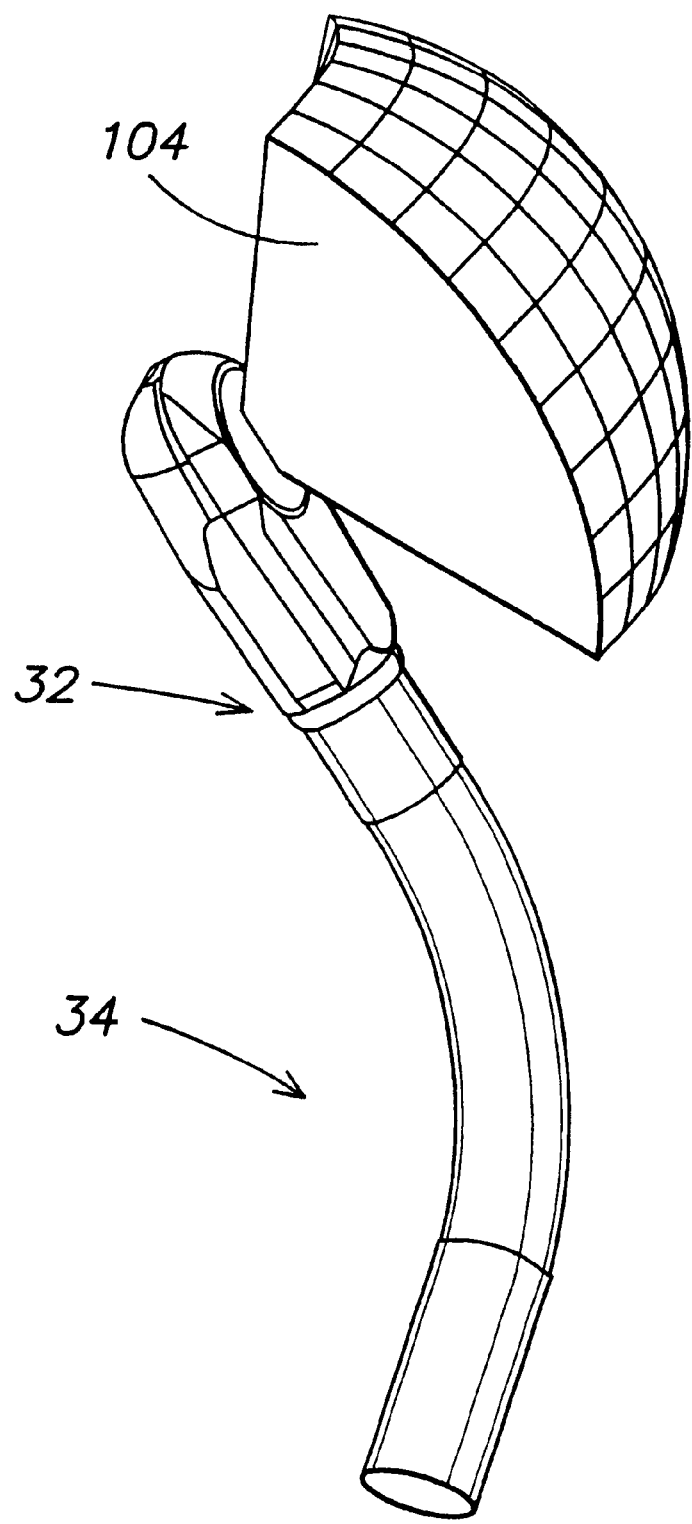
Figure 4D:
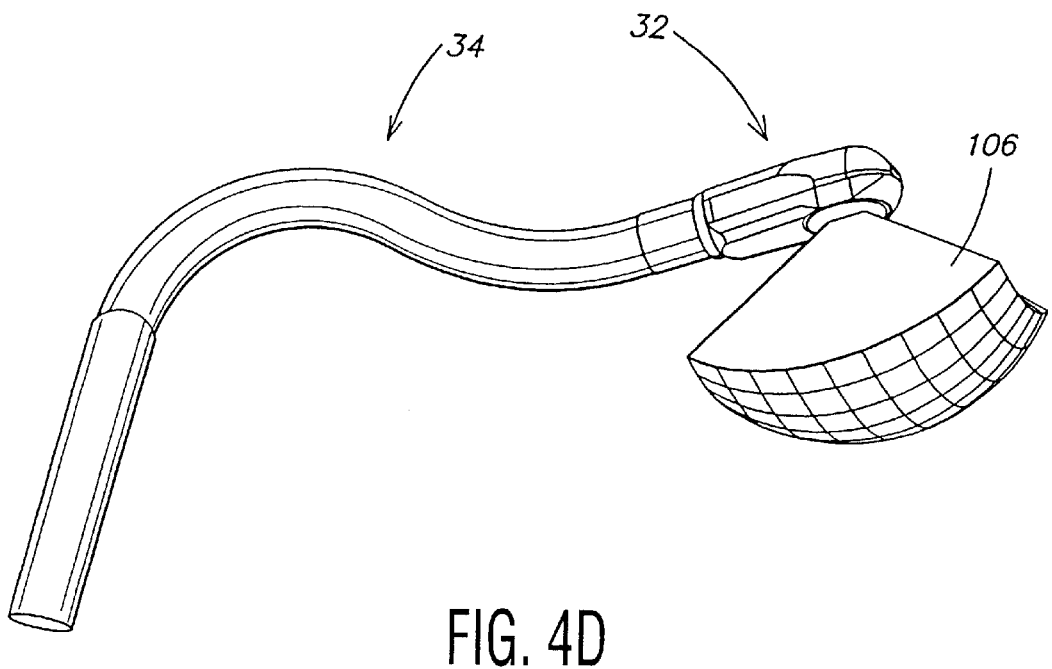
Figure 4E:
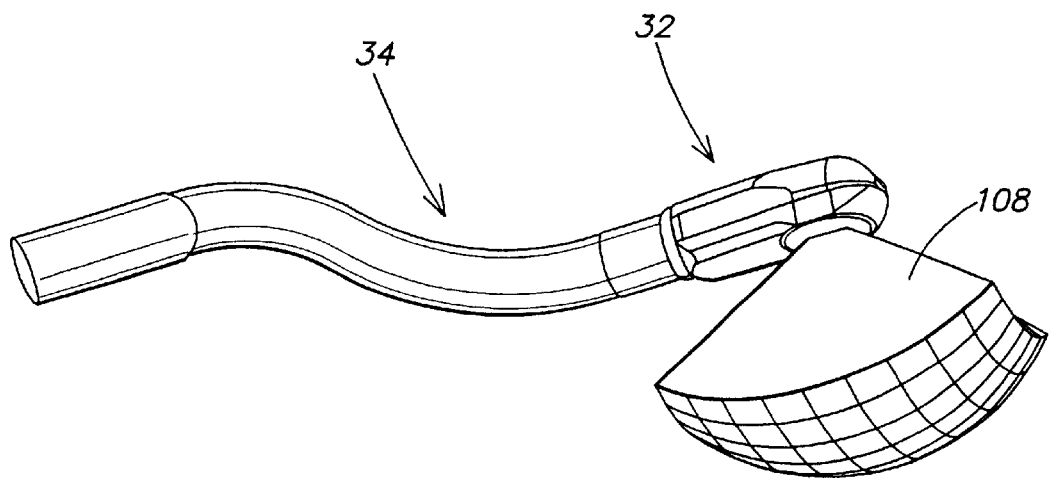

Referring to FIGS. 3 and 3A, rigid core region 32B of imaging core 40 includes a proximal housing 46 and a distal housing 48 shaped for rotational movement defined by one or several sets of bearings located inside rigid sheath region 32A (FIGS. 4–4B described below). Rigid region 32B also includes a transducer array 42 arranged to form a one-dimensional array (or 1.5 dimensional array) of ultrasonic transducer elements disposed linearly on imaging core 40. Transducer array 42 may include 2 to 256 transducer elements, and preferably includes 64 transducer elements. The transducer elements are connected to a flex circuit 56 extending inside drive shaft 50 and being connected to a cable connector 150 inside handle 14 (shown in FIG. 6). Flex circuit 56 is modified along flexible region 34B and along elongated core part 36B to have a low bending stiffness that is substantially uniform in all directions. For example, one or several flex circuit strips may be sliced along their length to expose the individual signal lines. The sliced strips are manipulated into a uniform radial distribution, and then potted in a flexible material (such as RTV or urethane). Alternatively, the transducer elements are connected to a multi-element, co-axial cable having a uniformly low bending stiffness. The co-axial cable extends inside drive shaft 50.

Drive shaft 50 is a tube-like structure that is torsionally stiff, but flexible for bending. Drive shaft 50 includes a steel coil 52 fitted tightly inside a silicon rubber or other biocompatible flexible tube 54. Coil 52 may be made of a metal or metal alloy wire and may be coated with a bio-compatible material. In a preferred embodiment, drive shaft 50 is made of three coils, each made from a beryllium copper flat coil 0.01 to 0.02 inch thick. These three flat coils are counterwound with respect to each other and have their turns interposed within each other. The coils are then fitted into a flexible biocompatible tube to achieve a unitary structure. When assembled, the coils are in a relaxed state and assume substantially the same diameter. This tube-like structure is torsionally stiff and is flexible for bending. Alternatively, drive shaft 50 includes a steel monocoil covered with a layer of a steel braid, and a polymer outer tube. The steel monocoil provides comprehensive strength to drive shaft 50, and the steel braid provides torsional stiffness.

FIGS. 4, 4A and 4B are cross-sectional views of different embodiments of steerable guide sheaths 60, 60A and 60B, respectively. A presently preferred embodiment is shown in FIG. 4. Steerable guide sheath 60 includes distal sheath part 30A and elongated part 36A connected to guide sheath adapter 15 of handle 14. Distal sheath part 30A has rigid sheath region 32A and flexible, articulation region 34A, which is described in detail below. Rigid region 32A includes a distal housing 62, two sets of bearings 64A and 64B molded into distal housing 62, an O-ring seal 68, and an ultrasonically transparent window 70. Transparent window 70 may be made of polyethylene. Distal housing 62 includes a fluid port 66 with a removable plug, an O-ring seal 67 (shown in FIGS. 5–5B) and bearings 64A located on its inner surface. The inner surface of distal housing 62 is also shaped to receive distal housing 48 (FIG. 3) of imaging core 40 in a manner that rigid core region 32B can rotate around its axis inside rigid sheath region 32A while being supported on, and restrained by, bearings 64A and 64B. O-ring seal 68 forms a seal between the outer surface of imaging core 40 and the inner surface of guide sheath 60. O-ring seal 68 provides a sealed transducer region extending from O-ring seal 68 to fluid port 66. The transducer region is filled with an ultrasonic coupling medium that acoustically couples transducer elements 42 (FIG. 3) to transparent window 70. Transparent window 70 may be made of polyethylene. Fluid port 66 provides access for introducing the coupling medium (e.g., Si oil, saline or water) into the transducer region. The outer surface of distal tip 62 is shaped for easy introduction and maneuverability of the catheter inside the vascular system.

As shown in FIG. 4, articulation region 34A includes a plurality of articulation links 72 displaced by one or several push-pull rods 74. Each push-pull rod is surrounded at least partially over its length by a spring sheath and connected at its proximal end to guide sheath adapter 15. Push-pull rod 74 is disposed in a channel 73 created inside articulation links 72 (FIG. 5C). As is described in connection with FIGS. 5, 5A and 5B, articulation links 72 together with push-pull rods 74 are constructed and arranged for easy articulation of flexible region 34A; this enables the advancement of the catheter inside the vascular system and the orientation of transducer array 42 relative to the examined tissue.

Guide sheath adapter 15 includes a housing 100, a V-band clamp actuator 102, a push-pull actuator 104 connected to a rack and pinion mechanism 106, and O-rings 108A, 108B and 108C. O-rings 108A, 108B and 108C seal guide sheath handle 15A to catheter handle 14, shown in FIG. 6. Specifically, O-rings 108A and 108B seal a surface 119A of a core housing 119, and ring 108C seals a surface 121A of a distal housing 121. When engaged, V-band clamp 102 locks sheath housing 100 in position relative to handle 14 and also limits the torque applied through O-rings 108A, 108B and 108C when imaging core 40 oscillates or rotates. An O-ring 107 seals push-pull actuator 104 to sheath housing 100. A rack and pinion mechanism 106, controlled by a push-pull actuator 104, displaces linearly push-pull rod 74. Alternatively, for example, a motor with an electronic actuator controlled by a joy stick may replace rack and pinion mechanism 106.

Referring to FIG. 4A, in another embodiment, a steerable guide sheath 60A includes a modified distal part 30B and elongated part 36A connected to a modified guide sheath adapter 15A. Distal part 30B has a modified rigid region 31 and flexible region 34A. Rigid region 31 includes a modified distal housing 61 with an open flush port 65, instead of fluid port 66 provided in rigid region 32A (FIG. 4) Similarly to rigid region 32A, rigid region 31 includes bearings 64A and 64B and transparent window 70. Similarly to guide sheath adapter 15, a guide sheath adapter 15A includes V-band clamp actuator 102, push-pull actuator 104 connected to rack and pinion mechanism 106, and O-rings 108A, 108B and 108C. Guide sheath adapter 15A also includes a flush port 110 connected to a sheath housing 100A. Flush port 110 is in communication with flush port 65. The introduced coupling medium (for example, hepranized saline solution) flows along the entire catheter length between the outer surface of imaging core 40 and the inner surface of catheter sheath 60A to flush port 65. In the transducer region, the coupling medium acoustically couples the transducer elements to transparent window 70.

Referring to FIG. 4B, in another embodiment, a steerable guide sheath 60B includes a modified distal portion 30C having a short rigid region 31A and flexible region 34A. Rigid region 31A includes a bearing housing 69 with a set of bearings 63A and 63B. Unlike in steerable guide sheaths 60 and 60A, rigid region 31A does not include the distal housing and the transparent window. A guide sheath adapter 15B is very similar to guide sheath adapter 15A and includes sheath housing 100A with V-band clamp actuator 102, push-pull actuator 104 connected to a rack and pinion mechanism 106, and O-rings 108A, 108B and 108C. The saline solution (or heparin) introduced at flush port 110 flows along the length of elongated part 36A between the outer surface of imaging core 40 and the inner surface of catheter sheath 60B and exits catheter sheath 60B at the proximal end of the transducer region. The saline solution and blood inside the vessel acoustically couple the transducer elements to the examined tissue.

Figure 5:
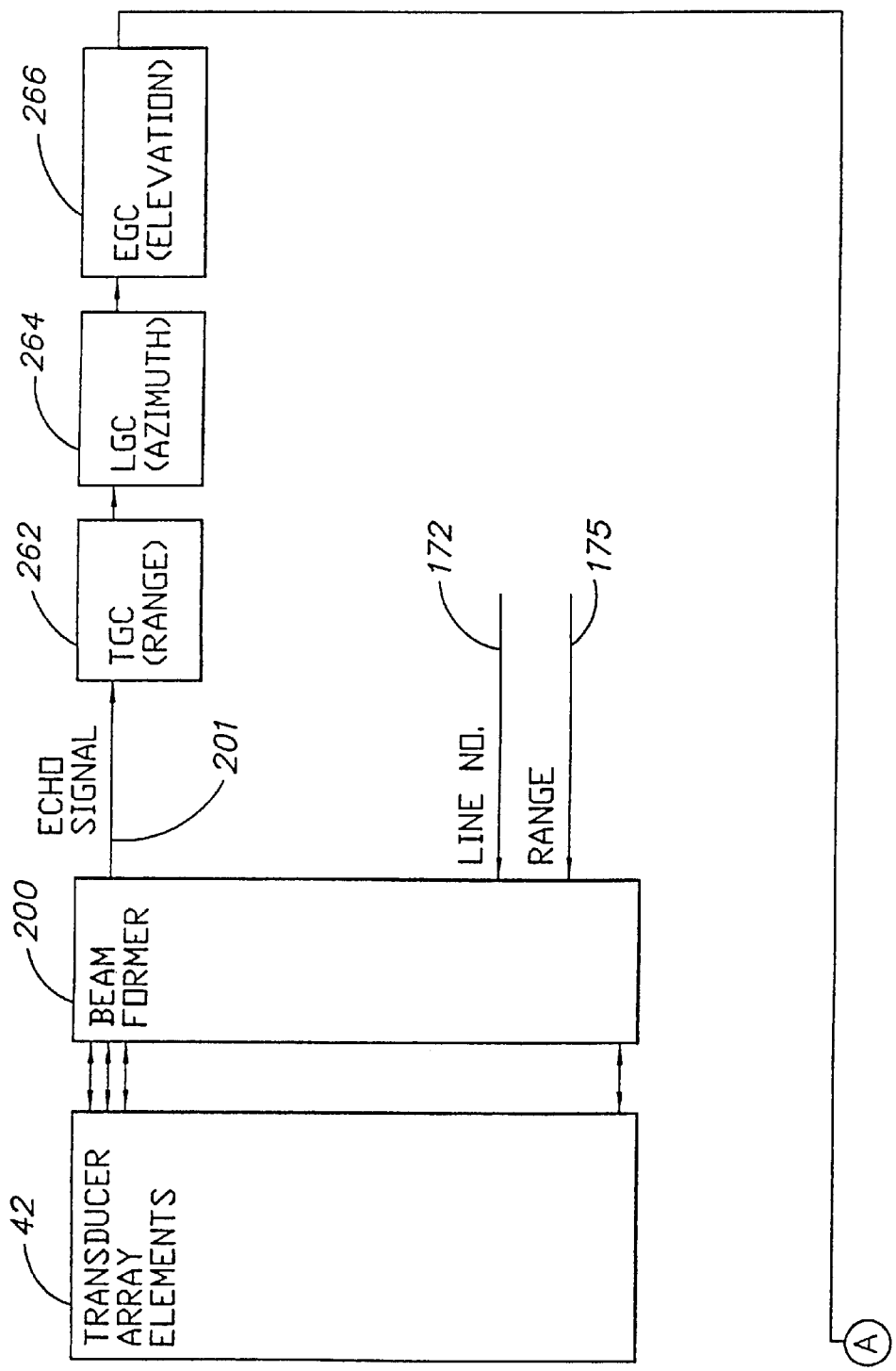
FIG. 5 shows the distal part of the steerable guide sheath articulated as an in-plane J hook.
Figure 5:
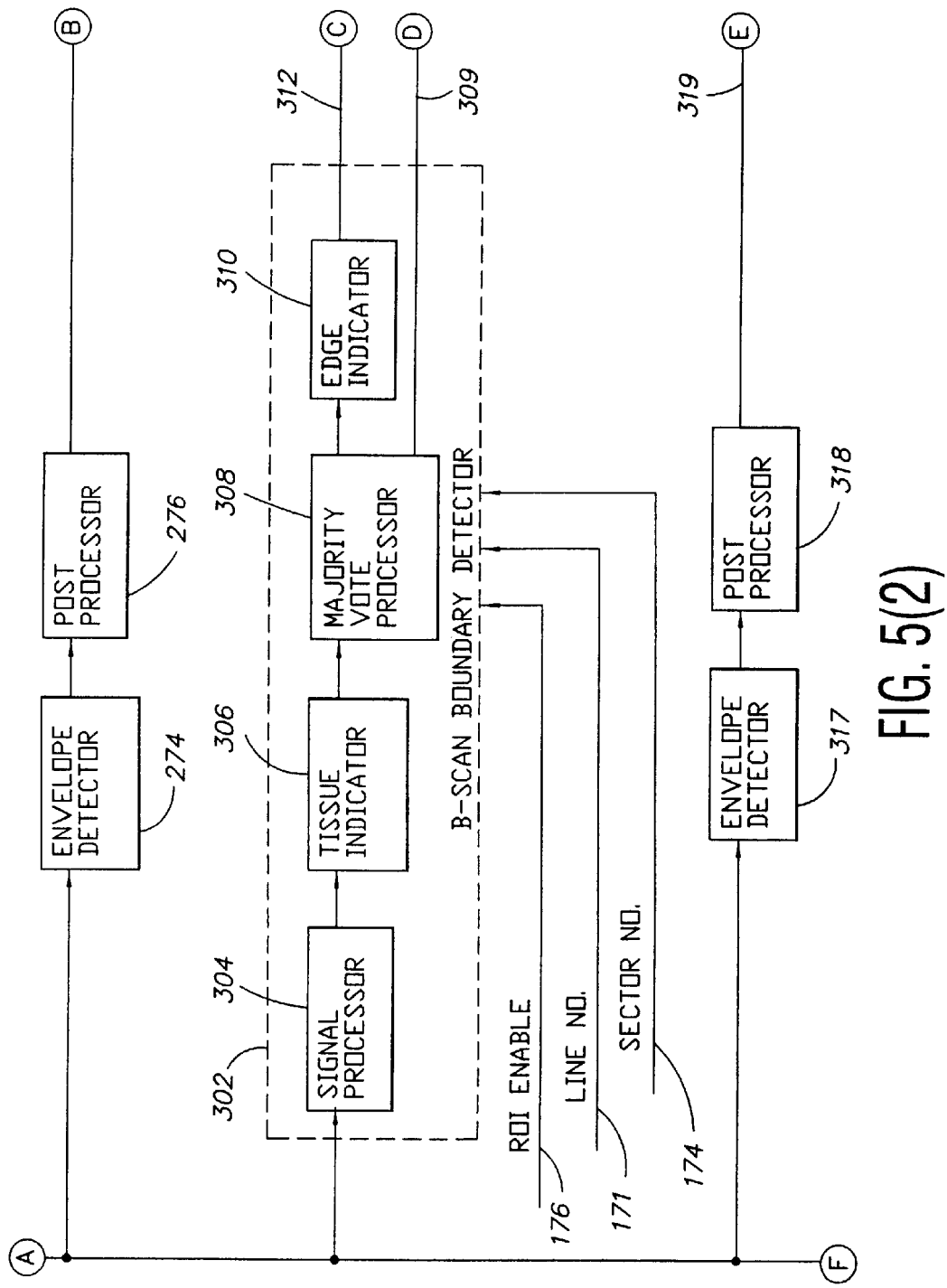
Figure 5:
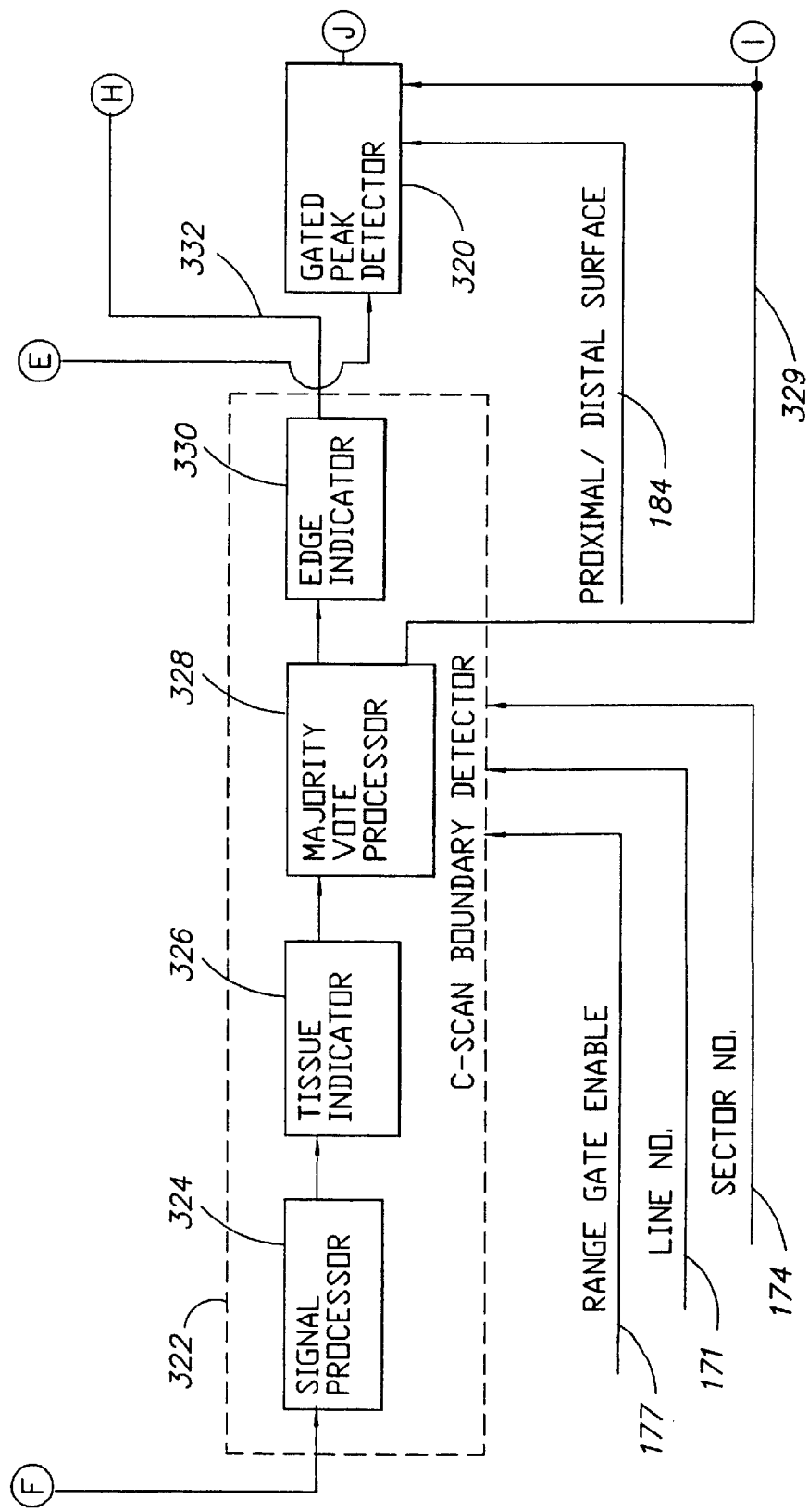
Figure 5:
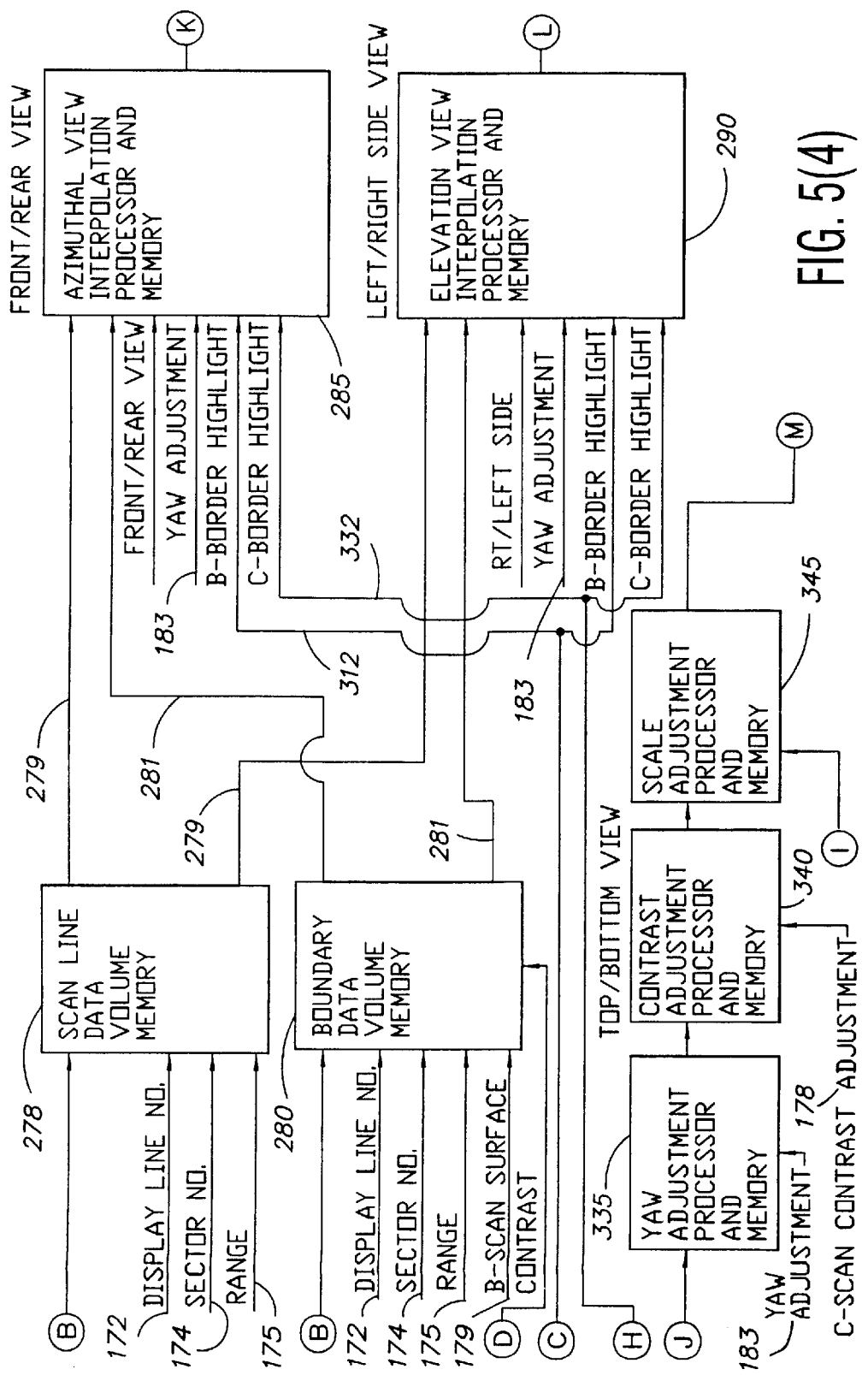
Figure 5:
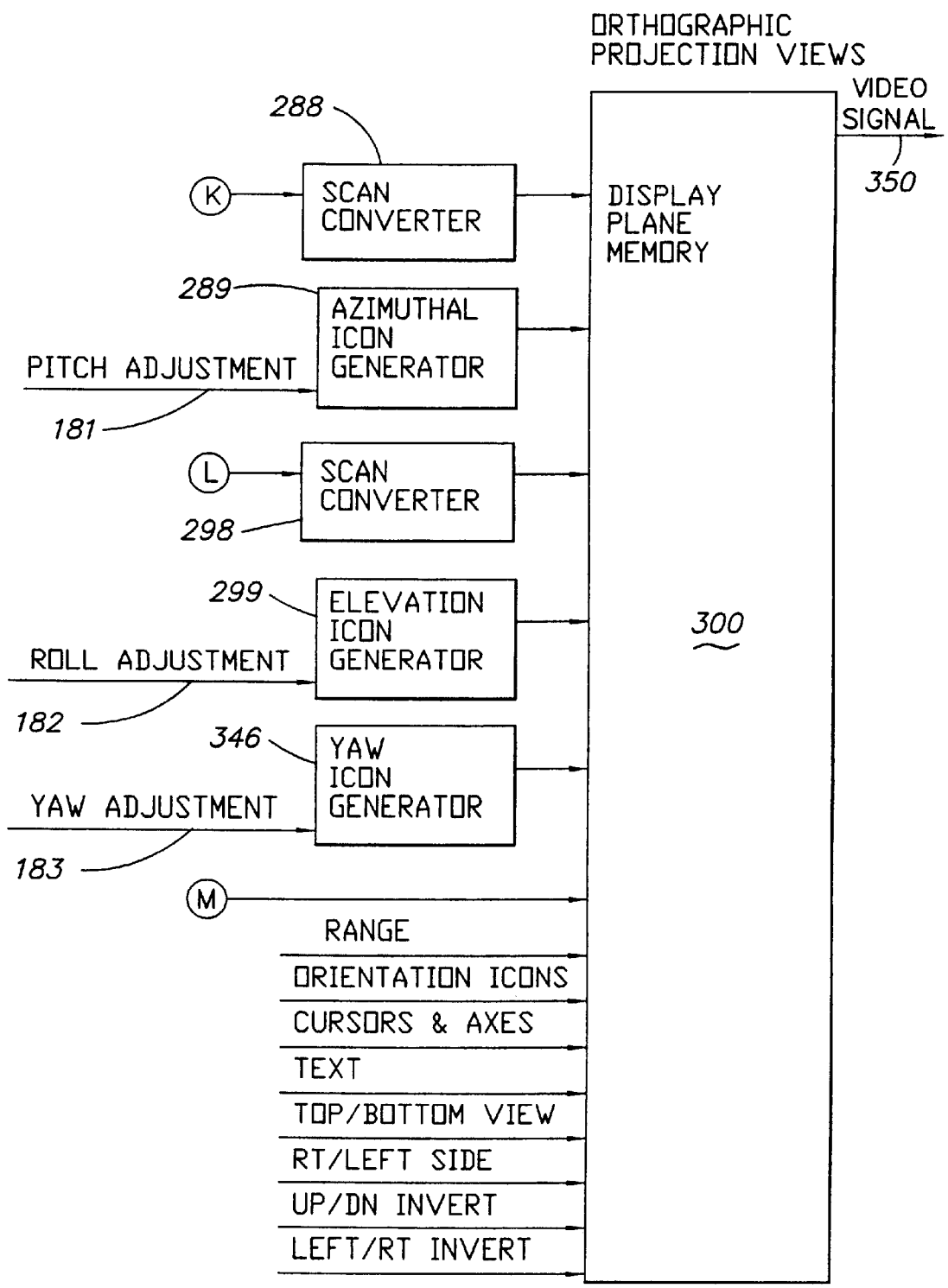
Figure 5A:
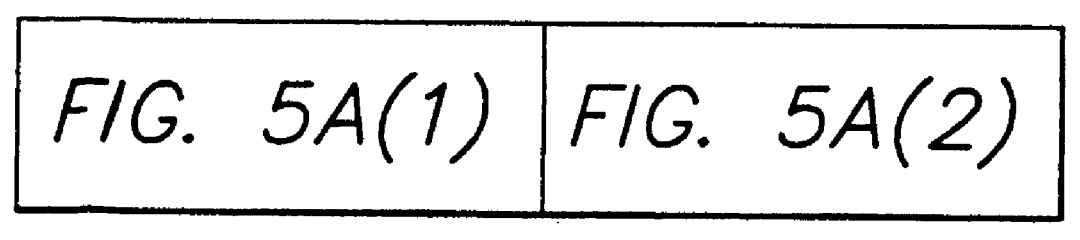
Figure 5B:
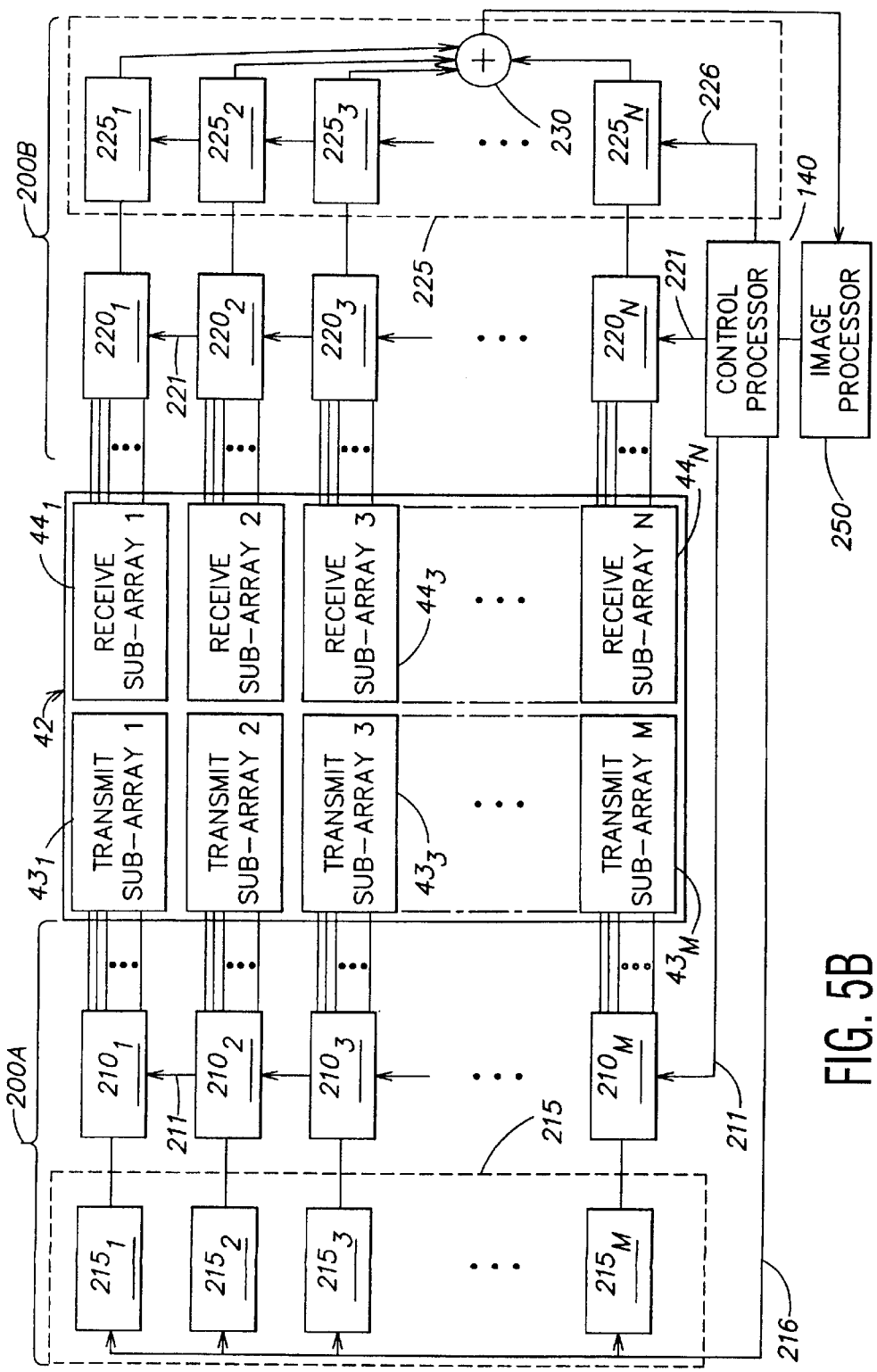
FIG. 5B shows the distal part of the steerable guide sheath articulated as an in-plane S hook.
Figure 5C:
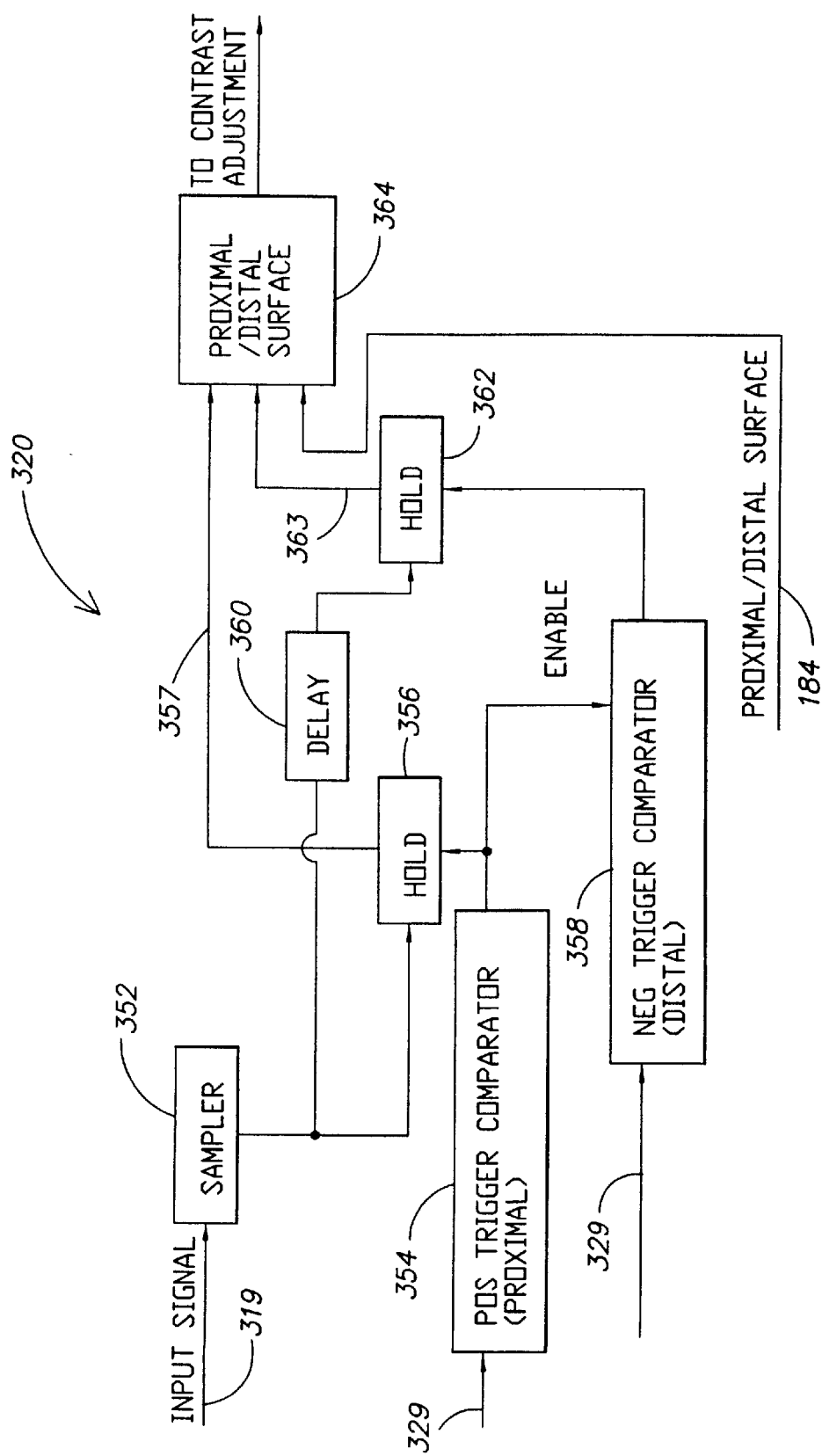
FIG. 5C is a perspective view of an articulation link used in the distal part of the steerable guide sheath.

FIGS. 5, 5A, and 5B show distal part 30A of the steerable guide sheath 60 articulated in various ways. Maneuverability of flexible region 34A relative to rigid region 32A enables both easy introduction and advancement of intravascular catheter 12 inside the vascular system, and positioning of transducer array 42 relative to the examined tissue. FIG. 5 shows distal part 30A articulated as an in-plane J hook. Flexible region 34A includes a proximal link 71, a set of links 72 (shown in detail in FIG. 5C), and a distal link 80 connected to the distal end of highly flexible pull-push rod 74 at a connection 75. When rack and pinion mechanism 106 (FIG. 4) displaces proximally push-pull rod 74, articulation region 34A bends and forms the in-plane J hook, wherein rigid region 32A and flexible region 34A are within the same plane. This in-plane bend is facilitated by the design of articulation link 72 cooperatively arranged with push-pull rod 74 connected to distal link 80 at its distal end.

Referring to FIG. 5C, articulation link 72 is a ring-like structure that includes a pivotable hinge connecting two neighboring links 72. The pivotable hinge includes two hinge pins 86A and 86B (not shown) disposed on the opposite sides of link 72 and extending from recessed surfaces 88A and 88B, respectively. Two hinge lips 90A and 90B include inside surfaces 91A (not shown) and 91B, which have a complementary shape to the shape of surfaces 88A and 88B (not shown). Two hinge lips 90A and 90B also include holes 92A and 92B, respectively, which are shaped to receive the hinge pins. Link 72 also includes a stop surface 94 and a stop surface 96. Stop surface 94 is positioned to provide a preselected maximum bending of articulation region 34A, facilitated by each link, upon the pulling action of push-pull rod 74. A stop surface 96 is positioned at a height that articulation region 34A to assume a straight orientation when push-pull rod 74 disposed in channel 73 does not pull on distal link 80. Alternatively, stop surface 96 may be designed for articulation region 34A to assume an opposite bend when push-pull rod 74 pushes on distal link 80.

FIG. 5A shows distal part 30A articulated as an out-of-plane J hook. Flexible region 34A includes proximal link 71, distal link 80 and another set of distal links 82. Push-pull rod 74 extends in channel 73 (FIG. 5C) from rack and pinion mechanism 106 (FIG. 4) to a connection 75 in link 80. Push-pull rod 76 extends from a distal end 77 through distal link 82 to another rack and pinion mechanism (not shown in FIG. 4) located in the guide sheath adapter. Proximally displaced push-pull rod 74 bends articulation region 34A. Push-pull rod 76 displaces distal link 82, connected to rigid region 32A, out of plane formed by flexible region 34A to achieve out-of-plane articulation of rigid region 32A; these two displacements for the out-of-plane J hook.

FIG. 5B shows distal part 30A articulated as an in-plane S hook. Flexible region 34A includes proximal link 71, sets of links 72A, an anchoring link 84, a set of links 72, and distal link 82 connected to rigid region 32A. Push-pull rod 74 extends from its distal end 75, connected to link 84, to rack and pinion mechanism 106 (FIG. 4) located in catheter adapter 15. Push-pull rod 78 extends from its distal end 79, connected to link 82, through links 72, link 84, links 72A and link 71 to another rack and pinion mechanism located in the catheter adapter. Links 72A are basically mirror images of links 72, but include two channels for accommodating push-pull rods 74 and 78. The two channels are located on the opposite sides of link 72A. Links 72 enable articulation in one orientation, and links 72A enable articulation in a 180 degree symmetric orientation. By proximally displacing push-pull rod 74, the rack and pinion mechanism actuates displacement of the proximal of part articulation region 34A in one direction. Furthermore, by proximally displacing push-pull rod 78, the rack and pinion mechanism bends the distal part of articulation region 34A in another direction, thereby forming the in-plane S hook. That is, the in-plane S hook has flexible region 34A and rigid region 32A located in the same plane.

The articulation region shown in FIG. 5B may be further modified to include push-pull rod 76 placed inside modified links 72 and 72A, as shown in FIG. 5A. By proximally displacing push-pull rod 76, articulation region 34A forms an out-of-plane S hook. The out-of-plane S hook has flexible region 34A located in one plane and rigid region 32A bend out of that plane. This arrangement enables both tilting transducer array 42 and pulling it back to achieve a desired distance from the tissue of interest.

Figure 6:
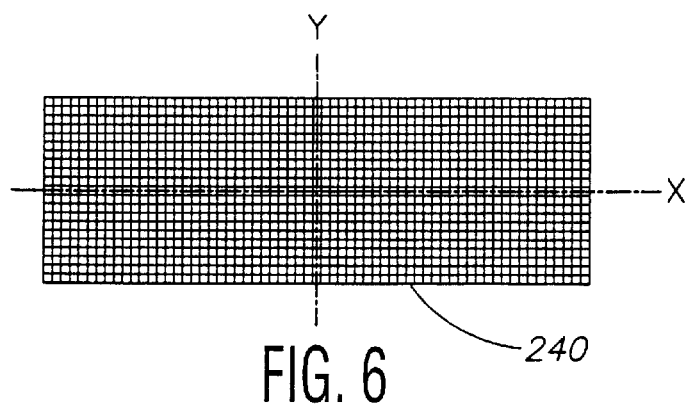
FIGS. 6A, 6B and 6C show diagrammatically drive elements inside the catheter of FIG. 6.

FIG. 6 is a cross-sectional view of catheter handle 14. Catheter handle 14 includes a distal housing 121 connected to a core housing 119, a set of controls 123 and a proximal housing 125 connected to strain relief 17. The elements inside catheter handle 14 are constructed and arranged to position and orient transducer array 42 relative to the examined tissue. Catheter handle 14 includes a drive motor 128 and a counter balance motor 138. Counter balance motor 138 is arranged to act opposite to drive motor 128 to eliminate undesired vibrations. Drive motor 128 drives a spline drive 130, which is connected to drive shaft 50. Spline drive 130 is suspended on a set of duplex pair ball bearings 132A and 132B, located within distal housing 121. Drive motor 128 is suspended on a set of bearings 134A and 134B, and counter balance motor 138 is suspended on bearings 140A and 140B. Flex circuit 56 extends inside drive shaft 50 into catheter handle 14 to a guide 142, beyond which it forms a service loop 144, connected to clamps 146 and 148. The proximal end of flex circuit 56 is connected to a connector 150, which provides connection to cable 16.

In a presently preferred embodiment, drive motor 128 is constructed and arranged to drive imaging core 40 at low oscillatory speeds or high oscillatory speeds depending on the imaging mode. In another embodiment, drive motor 128 and counter balance motor 138 are constructed and arranged to rotate imaging core 40 at low or high rotational speeds. A rotary encoder (for example, made by MicroMo Electronics, Clearwater, Fla.) senses the position of drive motor 128 and provides the data to a control processor.

Figure 6A:
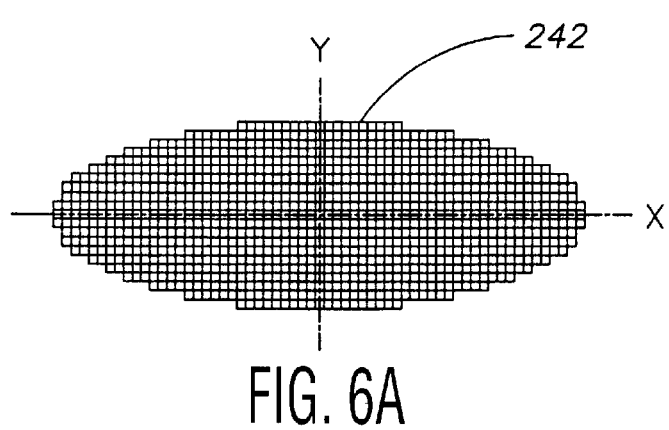
Figure 6B:
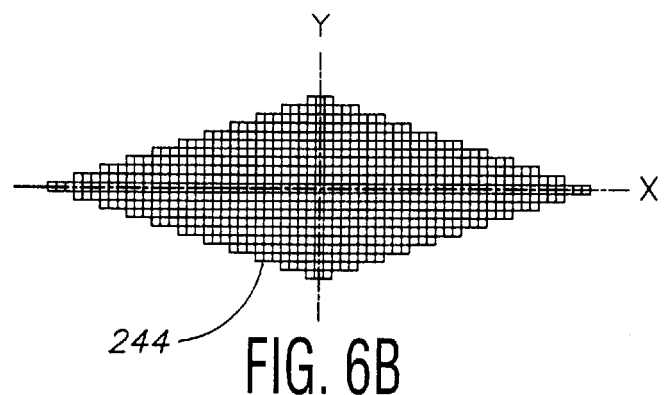
Figure 6C:
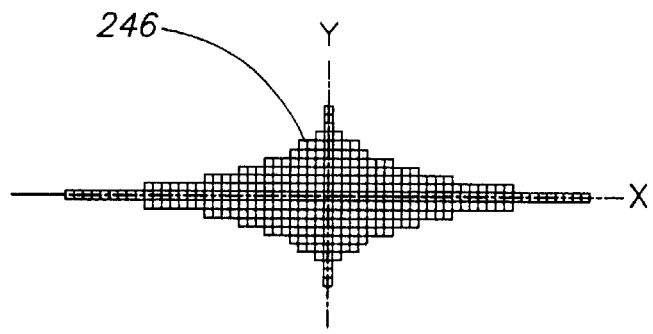

Referring to FIG. 6A, the vibration damping system, formed by drive motor 128 and counter balance motor 138, is designed to have a natural frequency response at the scanning frequency of transducer array 42. Counter balance motor 138 acts opposite to drive motor 128 to reduce substantially, or eliminate completely, the oscillation load onto handle 14. Load mass 154 with inertia $I_1$ represents imaging core 40 connected to drive motor 128 by a spring constant $K_1$. Damping constant $C_1$ represents the influence of catheter sheath 60 together with the saline solution onto the movement of imaging core 40. Spring constant $K_2$ and damping constant $C_2$ represent coupling of drive motor 128 via bearings 134A and 134B to handle housing 122 (FIG. 6). Handle 14 also includes a counter balance mass 156 with inertia $I_2$ attached to counter balance motor 138. Spring constant $K_3$ and damping constant $C_3$ represent coupling of counter balance motor 138 to handle housing 122 via bearings 140A and 140B. This system is tuned to operate at frequencies in the range of few Hz to 40 Hz, and preferably around 20 Hz.

FIG. 6A also shows diagrammatically a position sensor 160 located in distal part 30 of catheter 12 and arranged for detecting orientation of ultrasound array 42. Position sensor 160 is connected in a closed loop control of drive motor 128. Position sensor 160 may be an AC electromagnetic field tracking sensor (for example, three space Fastrak® made by Polhemus, Burlington, Vt.) or a DC electromagnetic field tracking sensor (for example, miniBIRD® made by Ascention Technology Corp., Burlington, Vt.). Alternatively, position sensor 160 may be an acoustic time-of-flight positioning system that uses ultrasound crystals imbedded in the distal tip of catheter 12 and one or several transmitters mounted on the patient. The time-of-flight system may use crystals from ultrasound array 42 detecting the transmitted signal, and a signal processor that performs the time-of-flight, positional conversion. For example, this system may be Sonomicrometer made by Sonometrics Corp., Ontario, Canada.

Handle 14 is connected to an accelerometer 162 made by Rieker Instrument Company, Folkcruft, Pa. (Model number SEIKA B2). Accelerometer 162 is arranged to detect unwanted shaking forces transmitted to the handle during high speed catheter movements. Drive motor 128 and counter balance motor 138 have a feedback control that affords an optimum arrangement for vibration control throughout a range of operational speeds and catheter to catheter variations without special internal tuning. Counterbalance control algorithms fine tune any variations in the load. Handle 14 includes control switches 123 (FIG. 6) for manually controlling the oscillation angle and frequency of transducer array 42. The oscillation angle and frequency can also be controlled by the imaging system depending on the examined tissue region and images already acquired, as described in connection with FIG. 7.

In one embodiment, imaging catheter 12 is connected to the phased array imaging system HP Sonos 2500 or HP Sonos 5500 (both previously manufactured by Hewlett-Packard Company, now Agilent Technologies, Inc., Andover, Mass.). The imaging system uses a phased array producing 121 scan lines for a 90° sector at a 60 Hz frame rate with an 8 cm depth. Transducer array 42 has 64 elements and has an elevation aperture of 2 mm and an azimuthal aperture of 6.5 mm. The elevation is not dynamically focussed when receiving echoes and does not have an adjustable transmit focus as the electrically scanned azimuthal array does. The elevation direction scan line sampling is more than 3.25 times coarser than the ¾ degree azimuthal sample spacing and elevation sample spacing of 3 degrees. The frame rate matches the oscillation rate of the array in the elevation direction and is about 20 Hz. By reducing the azimuthal angular range of each sector to about 30 degrees, the number of scan lines can be reduced to only 41 lines; this permits 9 sectors to be acquired for each frame in the elevation direction. This arrangement produces an elevation sector width of 24 degrees, which is 80% of the width in the azimuthal direction.

There are several advantages to positioning transducer array 42 near the examined tissue and performing near-in field imaging. When the targeted tissue is closer to the imaging catheter, the scan line spacing may be proportionally increased from the commonly used ¾ degree in the azimuth and 3 degrees in the elevation direction. The azimuth sector may be increased to 90 degrees and the elevation increases to 72 degrees. In addition, for a tissue region located only a few centimeters away (e.g., 1–3 cm), the imaging system may switch from the phased array imaging mode to the linear array imaging mode. The system can provide a combination of phase and liner array imaging having a trapezoidal display, as described in the U.S. patent application Ser. No. 08/665,521, which is incorporated by reference.

The three-dimensional ultrasound data acquired by catheter 12 may be processed using standard reconstruction algorithms such as algorithms described in U.S. Pat. No. 5,159,931. The three-dimensional data may also be processed using commercially available products, such as Compact 3d®, and displayed on a graphics work station Echo-View® made by TomTec Imaging Systems GmbH, Edisonstrasse 6, Unterchleissheim, Munich, Germany.

Figure 7:
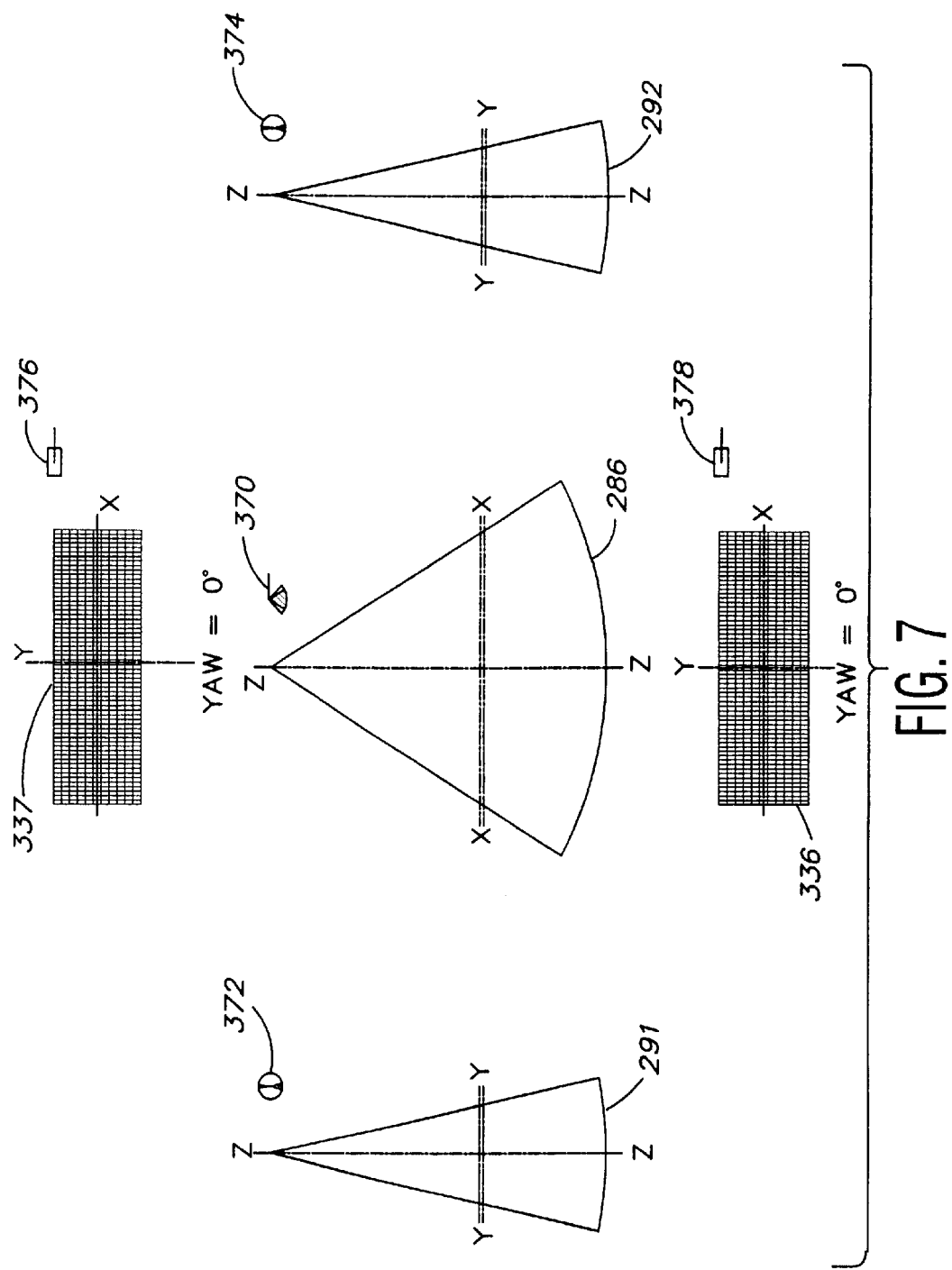
FIG. 7 shows an imaging volume of echo data used to illustrate orthographic projection views.

Alternatively, the imaging system generates several orthographic projection images described below. FIG. 7 shows an imaging volume V of data collected by transducer array 42. Transducer array 42 emits ultrasound lines over an azimuthal angular range, detects echoes over a selected radius (R) and an azimuthal angular range ($\theta=\pm 45°$) to acquire ultrasound data for one image plane. To image a tissue volume, drive motor 128 oscillates transducer array 42 about its axis over an elevational angular range ($\Phi=\pm 30°$). Thus, imaging volume V includes several image planes, called image sectors (labeled as $S_{-1}$, $S_{-2}$, $S_{-3}$, $S_0$, $S_1$, $S_2$ and $S_3$).

Figure 9C:
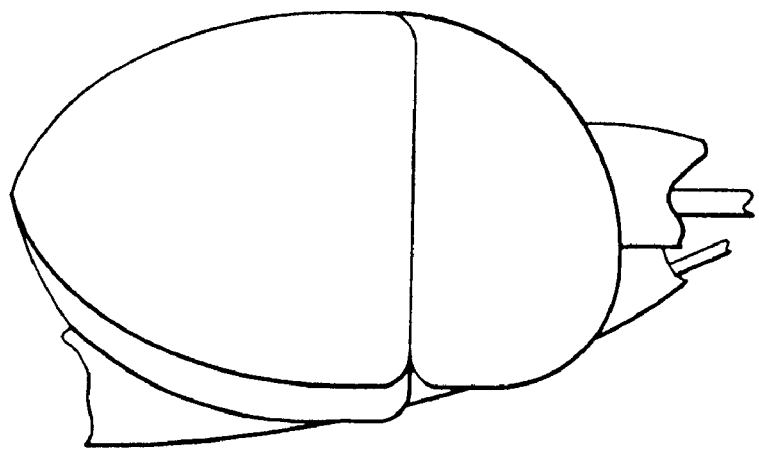
FIG. 9 illustrates five orthographic projection views provided by the ultrasound imaging system of FIG. 1.
Figure 9D:
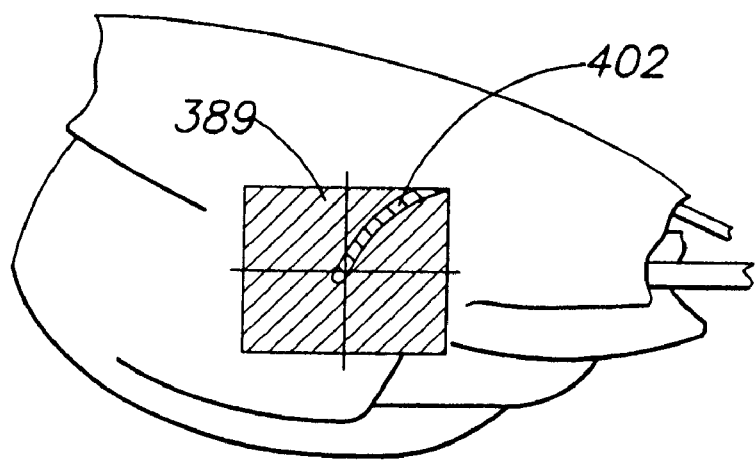

Referring also to FIG. 9, the imaging system can display three orthographic projection views that are within two orthogonal central planes $S_0$ and $L_0$ (FIG. 7) having a zero degree azimuthal and elevational location, respectively. When image sector $S_0$ (with elevation angle 0 degrees) is imaged from y=∞ toward y=0, it is called a front view 286. A rear view (not shown) is imaged from y=-∞ toward y=0. The image sectors located at $L_0(\theta=0°)$ imaged from x=∞ toward x=0 and x=-∞ toward x=0 are called the right side view 292 and the left side view 291, respectively. At this point, the clinician can re-select scan parameters or display parameters as described below.

The imaging system initially provides the front view and the side views to a clinician. The imaging system also provides at least one modified C-scan image that is an image of a selected surface perpendicular to the front and side view planes over the scanned volume, V. The modified C-scan image displaying a tissue surface projecting from z=0 is called the top view 337, and the C-scan image displaying a tissue surface on the other side (from z=∞) of the C-scan plane is the bottom view 336. A clinician can manually select (or the system can select automatically) the surface to be shown in the modified C-scan image. The imaging system generates these orthographic projection images in real time, at a frame rate above 15 Hz (and preferably in the range of about 20 Hz to 60 Hz).

The imaging system provides six degrees of freedom to adjust the image.

The electronic adjustment provides three degrees of freedom to obtain a selected view orientation. Three additional degrees of freedom come from the spatial orientation of transducer array 42 relative to a selected tissue structure. Transducer array 42 is oriented by articulating articulation region 34 as shown in FIGS. 5 through 5B. The articulation alters orientation of the imaging volume and thus the orientation of the front, side, and bottom views.

FIGS. 7A through 7F show examples of different orientations of the imaging volumes collected by imaging catheter 12 having the catheter articulations described in connection with FIGS. 5 through 5B. FIG. 7A shows an imaging volume 165 collected by imaging catheter 12 having flexible region 34 (flexible sheath region 34A in FIG. 2) extended straight. Transducer array 42 oscillates around the visual apex of the acquired image sector, since bearings 64A and 64B in catheter sheath 60 (FIG. 4) confine rigid region 32B to rotate about its center line. Transducer array 42 provides image sectors 167A, 167B, 167C, 167D, 167E, 167F and 167G by oscillating about an elevation range of ±30 degrees.

FIG. 7B shows an imaging volume 168 collected by the imaging system having flexible region 34 articulated to form the in-plane J hook shown in FIG. 5. FIG. 7C shows an imaging volume 170 generated by the imaging system with flexible region 34 articulated to form the out-of-plane J hook shown in FIG. 5A. FIGS. 7D and 7E depict imaging volumes 172 and 174 generated by the imaging system when flexible region 34 is articulated as the S hook (shown in FIG. 5B), and the in-plane J hook combined with the out-of-plane J hook, respectively. FIG. 7F depicts imaging volume 178 collected by the imaging system having flexible region 34 articulated as the S hook and the in-plane J hook.

Advantageously, the above-described arrangements provide views that are always predictable, from one elevation position of transducer array 42 to another, as the image plane always rotates about the image apex on a video display (described in detail below). The acquired images are, therefore, more easily understood by a clinician, as opposed to non-constrained rotational arrangement of an ultrasound array where rotational pivot points are not predictable from one image position to another. The present arrangement also provides a platform for generating the various three-dimensional imaging modes described below.

Figure 8:
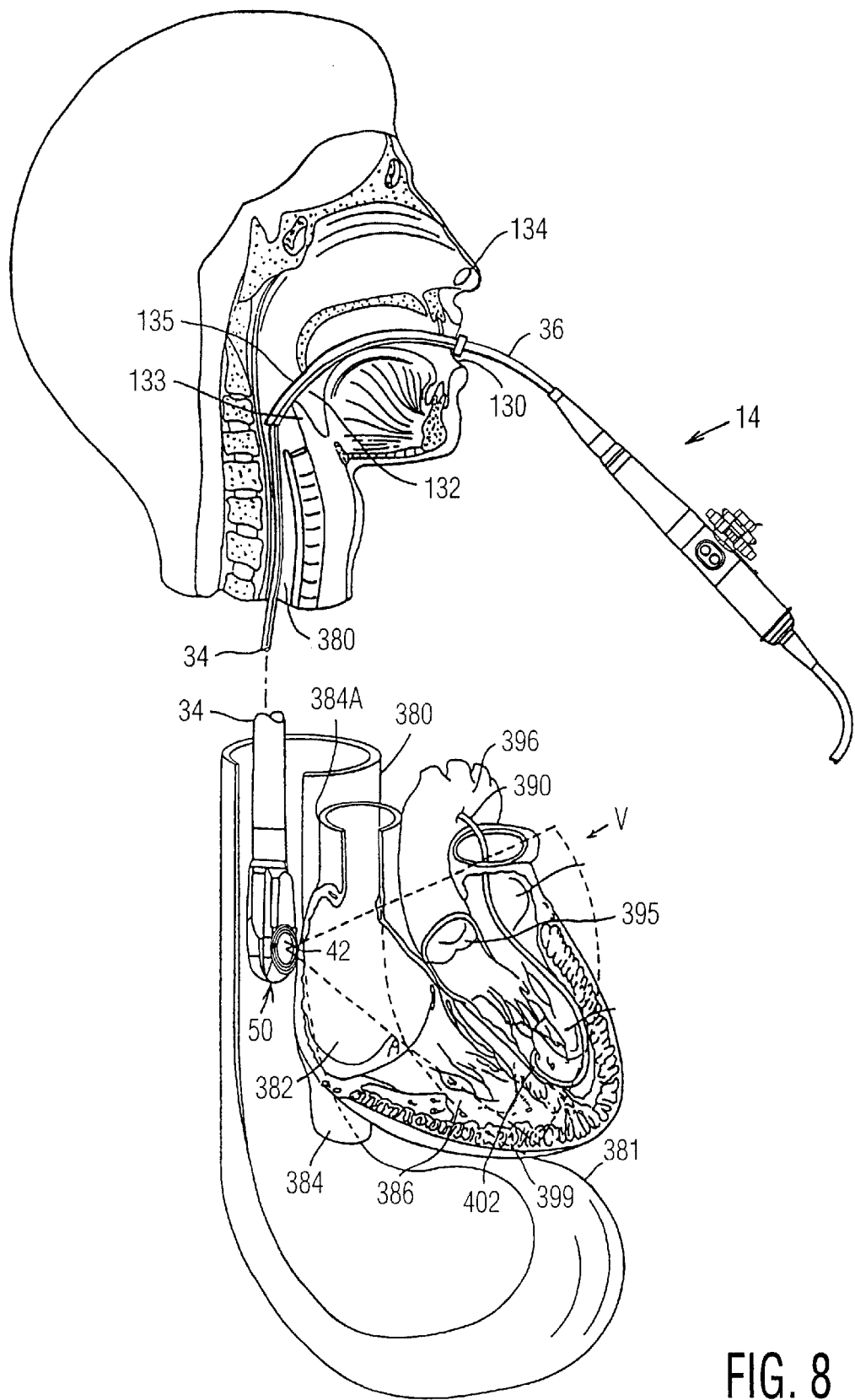
FIGS. 8 and 8A show diagrammatically a preferred embodiment of the ultrasound system of FIG. 1.
Figure 8A:
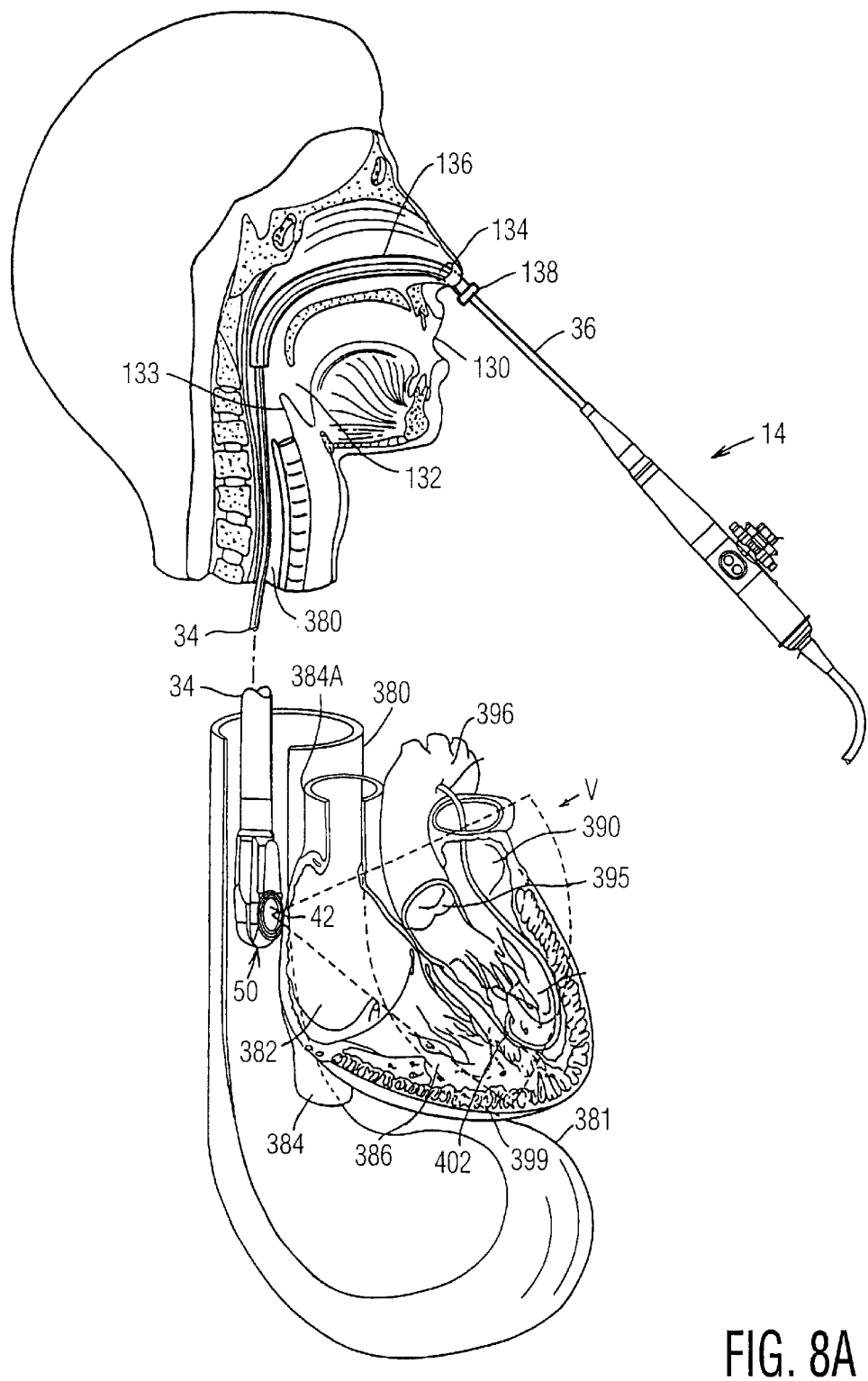

FIGS. 8 and 8A show diagrammatically the imaging system according to a presently preferred embodiment. The entire operation of the imaging system is controlled by a control processor 200. Control processor 200 receives input commands from input controls 202 through 227 and provides output control signals 230 through 251. Control processor 200 provides control data to a servo motor encoder and controller 255, and a beamformer 260, and provides image control data to processing and display electronics.

To control the elevation orientation of array 42, servo motor encoder and controller 255 receives control data defining elevation sector angle 233 and an elevation sector number 234. Furthermore, controller 255 receives data from position sensor 160 (FIG. 6A). Controller 255 drives motor 128 (FIG. 6) that displaces transducer array 42 to a desired elevation angle and then the system collects the scan data for this image sector. (Alternatively, transducer array 42 acquires the scan data over several sectors while being continuously displaced over a selected elevation range).

To control scanning within an image sector, control processor 200 provides the control data, such as timing 230, a scan line number 231 and a range 235, to beamformer 260. Beamformer 260 includes a transmit beamformer and a receive beamformer. The transmit beamformer directs transmission of the ultrasound beam along selected scan lines. Preferably, in this embodiment, the transmit beamformer phases the transmission from the transducer elements to emit the ultrasound beam along several transmit scan lines spaced over a selected angular distribution in a pie-shaped sector. In the receive mode, the receive beamformer phases the transducer elements to detect the ultrasound echoes along one or several receive scan lines spaced over a selected angular distribution. The operation of the transmit and receive beamformers connected to a phased array is described, for example, in U.S. Pat. Nos. 4,140,022; 4,893,283; 5,121,361; or 5,469,851.

To define parameters of the B-scan, control processor 200 receives input data defining a sector scan depth 208, a frame rate 210, and an azimuth/elevation scan ratio 212. The sector scan depth defines the range (R) over which the echoes are detected, for example, 4 centimeters, 8 centimeters, or 10 centimeters, depending on the location of the transducer array relative to the biological tissue of interest. The clinician can select frame rate 210 depending on the tissue structures of interest. For real-time images of a moving organ, the frame rate has to be at least several frames per second to avoid blurring of the image due to the movement of the tissue. The user also selects azimuth/elevation scan ratio 212, which varies the B-scan from a large azimuth scan (i.e., a large angular range of the scan lines within image sector) of a single sector to a minimum azimuth scan performed over a large number of sectors (i.e., a small angular range for each sector scanned over a large elevation displacement.) Thus, azimuth/elevation scan ratio 212 provides a bottom view image aspect ratio (i.e. x/y dimension) of bottom view 336 and a top view aspect ratio of top view 337 for the C-scan, as shown in FIG. 9.

Depending on the preferred sector scan depth, the frame rate, and the azimuth/elevation scan ratio, control processor 200 calculates the angular spacing between the scan lines and the number of scan lines (231) for each sector. Based on the initial values, processor 200 allocates the largest possible number of scan lines and the largest possible number of sectors. Specifically, processor 200 calculates the angular spacing between the scan sectors, that is, a sector angle (233) and the number of sectors (234). Control processor 200 provides these values to beamformer 260 and controller 255 as described above.

Control processor 200 selects the scanning sequence performed by beamformer 260. The transmit beamformer directs emission of the phased ultrasound beam along the scan lines over the ranges calculated for each sector. For each emitted scan line, the receive beamformer phases the transducer elements to detect the ultrasound echoes along a corresponding receive scan line. Alternatively, the receive beamformer synthesizes the scan data from several receive scan lines that are spaced over a selected angular distribution as is described, for example, in the U.S. application Ser. No. 09/046,437 entitled "Increasing the Frame Rate of a Phased Array Imaging System," which is incorporated by reference.

The RF data is filtered by a filter with a pass band of as much as 60% around the center frequency of as high as 10 MHz, or preferably a pass band of about 35% around the center frequency in the range of about 5 MHz to 7 MHz.

Control processor 200 receives a time gain compensation (TGC) input 202, a lateral gain compensation (LGC) input 204, and an elevation gain compensation (EGC) input 206 entered by a clinician or stored in a memory. The TGC control adjusts the receive channel gain, usually in discrete steps, as a function of the distance from the transducer array. The TGC control compensates for attenuation of ultrasound waves as they propagate through the medium. The LGC control varies the receive channel gain as a function of the azimuthal displacement of a particular scan line, while the gain along the scan line remains unaffected with the distance from the transducer array. The LGC control is desirable where the ultrasound signal decreases in a particular region due to the anatomical structure of the tissue, or where tissue orientation in the subject results in echo signals having varying brightness. The EGC control varies the receive channel gain as a function of the elevational displacement, i.e., adjusts the gain for a selected scan sector (i.e., scan plan). The user can also re-adjust the TGC, LGC and EGC manually so that the image "looks" better.

The receive beamformer provides detected RF signals to a time gain compensator (TGC) 262, a lateral gain compensator (LGC) 264, and an elevation gain compensator (EGC) 266, which perform the corrections described above. The EGG 266 provides the compensated data to boundary detectors 302 and 322.

Alternatively, the TGC 262, the LGC 264 and the EGC 266 are replaced by a rational gain compensation (RGC), which is described in U.S. Pat. No. 5,195,521 and in "Rational Gain Compensation for Attenuation in Cardiac Ultrasonography," *Ultrasonic Imaging*, Vol. 5, pp. 214–228 (1983). The RGC compensates for attenuation while distinguishing between blood and cardiac tissue. The RGC varies the signal gain for blood and cardiac tissue by using a threshold value below which the backscattered signal is defined as "zero." In this case, the backscattered signal is arriving from blood.

Referring still to FIG. 8A, post processors 276 and 318 receive filtered and compensated data from envelope detectors 274 and 317. Post processors 276 and 318 control the contrast of each data point by mapping the data onto a set of selected curves. After assigning a contrast level to each data point, a scan line buffer may be used to hold temporarily the data of one scan line.

A scan line data volume memory 278 receives the processed echo data and also receives from processor 200 display line number 232, sector number 234, and range 235. Data volume memory 278 stores the data in a matrix form by assigning a number to each sector and another number to each scan line in the azimuthal direction. The size of the data matrix stored in data volume memory 278 depends upon the acoustic frame rate. Each scan cycle (i.e., acoustic frame) fills the data matrix with the data acquired over the scan volume delineated by the azimuthal range and the elevation range. The scan line number corresponds to the column number in the data volume matrix. The sector number corresponds to the row number in the data volume matrix. The range data corresponds to the column height in the data volume matrix. Data volume memory 278 provides its output 279 to processors 285 and 290.

Similarly, a boundary data volume memory 280 also receives the processed echo data and data from a majority vote processor 308. Boundary data volume memory 280 also receives from processor 200 display line number 232, sector number 234, range 235 and B-scan surface contrast 239. Data volume memory 280 also stores the data in a matrix form. Data volume memory 280 provides its output 281 to processors 285 and 290.

An azimuthal view interpolation processor 285 and an elevation view interpolation processor 290 receive data from memory 278 and memory 280 and receive data from B-scan edge indicator 310 and C-scan edge indicator 330. Depending on the view input, the interpolation processors 285 and 290 generate the selected front view and the selected side view, respectively. The front and side views are provided to a display plane memory 300, which in turn provides a video signal 350 to a video display. Based on the front view or the side view (B-scan data), a clinician can select a region that includes a selected tissue region. The clinician selects the tissue of interest either by setting range gates or by drawing a region of interest (ROI) around the imaged tissue.

A clinician can outline a region of interest based on the front view and the side view (i.e. the B-scan image). Control processor 200 transforms an ROI perimeter input 213 into a range 235, ROI markers and gates 236. They can be displayed on the video display to outline a region. They are also provided to boundary detector 302 and boundary detector 322 to perform boundary detection in response to echoes from points within the ROI. Usually, a tissue surface or structure undulates in and out of a single plane or range. By simply displaying echo data by only selecting a range value or a region of interest could result in a random patchwork of areas that a clinician would find difficult to visualize or understand. Thus, the system uses a B-scan boundary detector 302 and a C-scan boundary detector 322 for finding the tissue surfaces of interest.

As shown in FIG. 8A, B-scan boundary detector 302 includes a signal processor 304, a tissue indicator 306, a majority vote processor 308, and an edge indicator 310. U.S. Pat. No. 5,195,521, which is incorporated by reference, discloses a majority vote circuit and circuits for generating the ROI. Control processor 200 provides to boundary detector 302 ROI enable output 236, line number output 231, and sector number output 234. Signal processor 304 derives from the RF data a characteristic sensitive to the difference between the echo from tissue and from blood in order to increase the accuracy of locating the tissue boundary. The characteristic is the amplitude of integrated backscatter from tissue and from blood. Signal processor 304 determines the amplitude of the integrated backscatter and provides it to tissue indicator 306. (Alternatively, tissue indicator 306 may receive the echo RF data directly.)

Tissue indicator 306 outputs a signal that is equal to either one or zero depending on whether the echoes are from tissue or blood. Majority vote processor 308 determines whether the majority of the signals are zero or one for the individual scan lines within a scan sector. That is, majority vote processor 308 produces, at each range, a signal indicative of whether the signal provided by the tissue indicator 306 represents echoes from tissue or blood majority vote processor 308 produces this signal for a majority of consecutive scan lines including the line currently being scanned. If indicator 306 outputs for a majority of the lines a signal indicating that reflections at a range are from tissue, majority processor 308 outputs a signal indicative of the fact that the reflections are from tissue. Similarly, if tissue indicator 306 outputs a different signal for a majority of lines, majority processor 308 outputs another signal indicative of the fact that the reflections are from blood.

Edge indicator 310 responds to a change in the signal provided by majority vote processor 308 to produce short pulses that are used to form an outline of cavities or ventricles in the image. Specifically, edge indicator 310 includes an edge indicator circuit (disclosed in U.S. Pat. No. 5,195,521) that outputs a high logic level for, e.g., 1 microsecond whenever the output of majority vote processor 308 changes from a high level to a low level and vice versa. The output 312 from edge indicator 310 is provided to processors 285 and 290 for highlighting B-scan borders. Furthermore, the output 309 from majority vote processor 308 is provided to boundary data volume memory 280 as described above.

C-scan boundary detector 322 operates similarly as B-scan boundary detector 302. C-scan boundary detector 322 includes a signal processor 324, a tissue indicator 326, a majority vote processor 328, and an edge indicator 330. Control processor 200 provides to boundary detector 322 a range gate enable output 237, line number output 231, and sector number output 234. Signal processor 324 derives from the RF data the amplitude of integrated backscatter from tissue and from blood and provides it to tissue indicator 326. Tissue indicator 326 outputs a signal that is equal to either one or zero depending on whether the echoes are from tissue or blood. Majority vote processor 328 determines whether the majority of the signals are zero or one for the individual scan lines within a scan sector. That is, majority vote processor 328 produces, at each range, a signal indicative of whether the signal provided by the tissue indicator 326 represents echoes from tissue or blood.

As described for edge indicator 310, edge indicator 330 responds to a change in the signal provided by majority vote processor 328 to produce short pulses that are used to form an outline of cavities or ventricles in the image. Specifically, edge indicator 330 outputs a high logic level whenever the output of majority vote processor 328 changes from a high level to a low level and vice versa; that is, the detected echoes change from tissue to blood and vice versa. The output 332 from edge indicator 330 is provided to processors 285 and 290 for highlighting C-scan borders. Furthermore, the output 329 from majority vote processor 328 is provided to a gated peak detector 320.

Figure 8B:
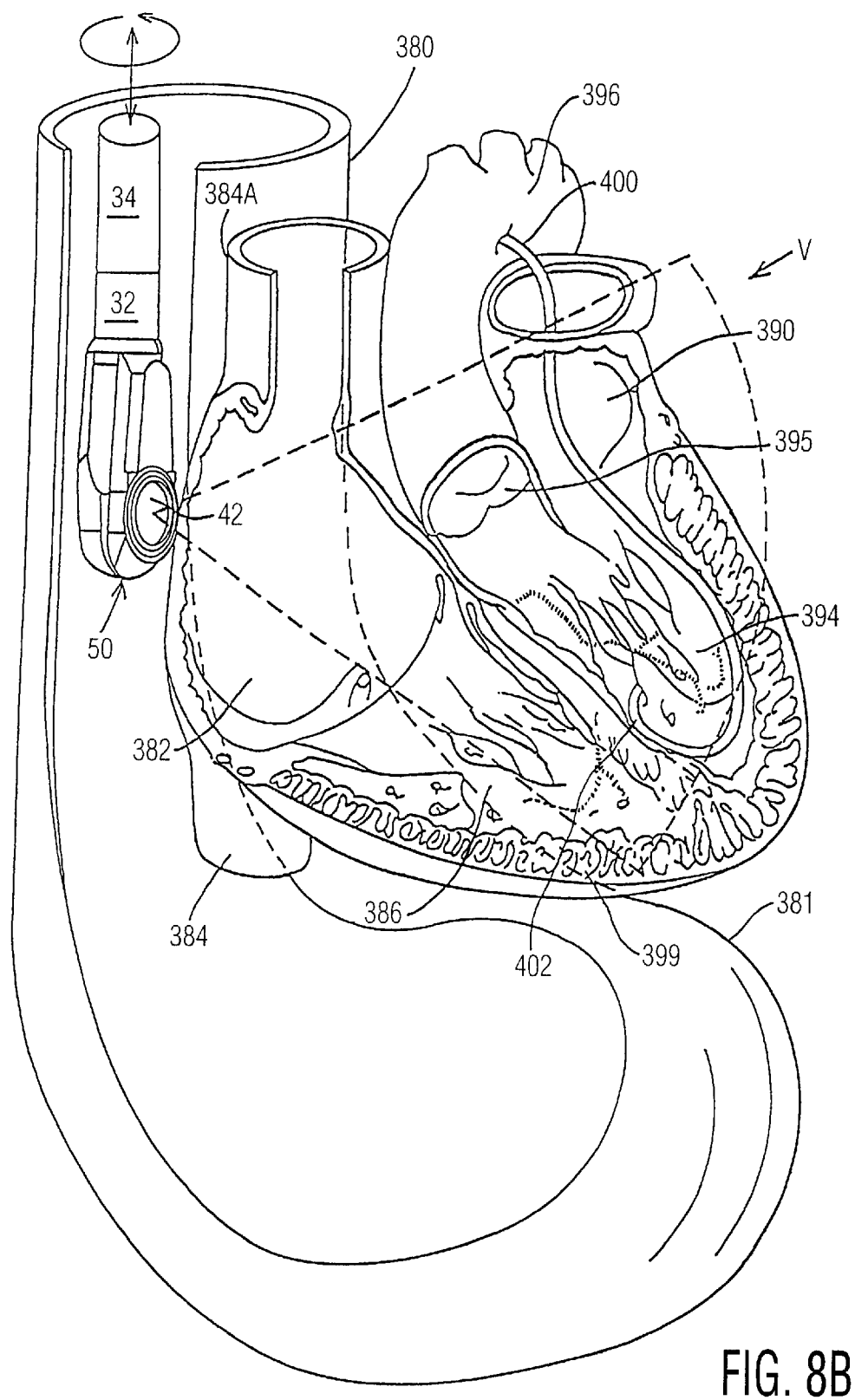
FIGS. 8B and 8C show diagrammatically a gated peak detector used in the ultrasound system shown in FIG. 8.
Figure 8C:
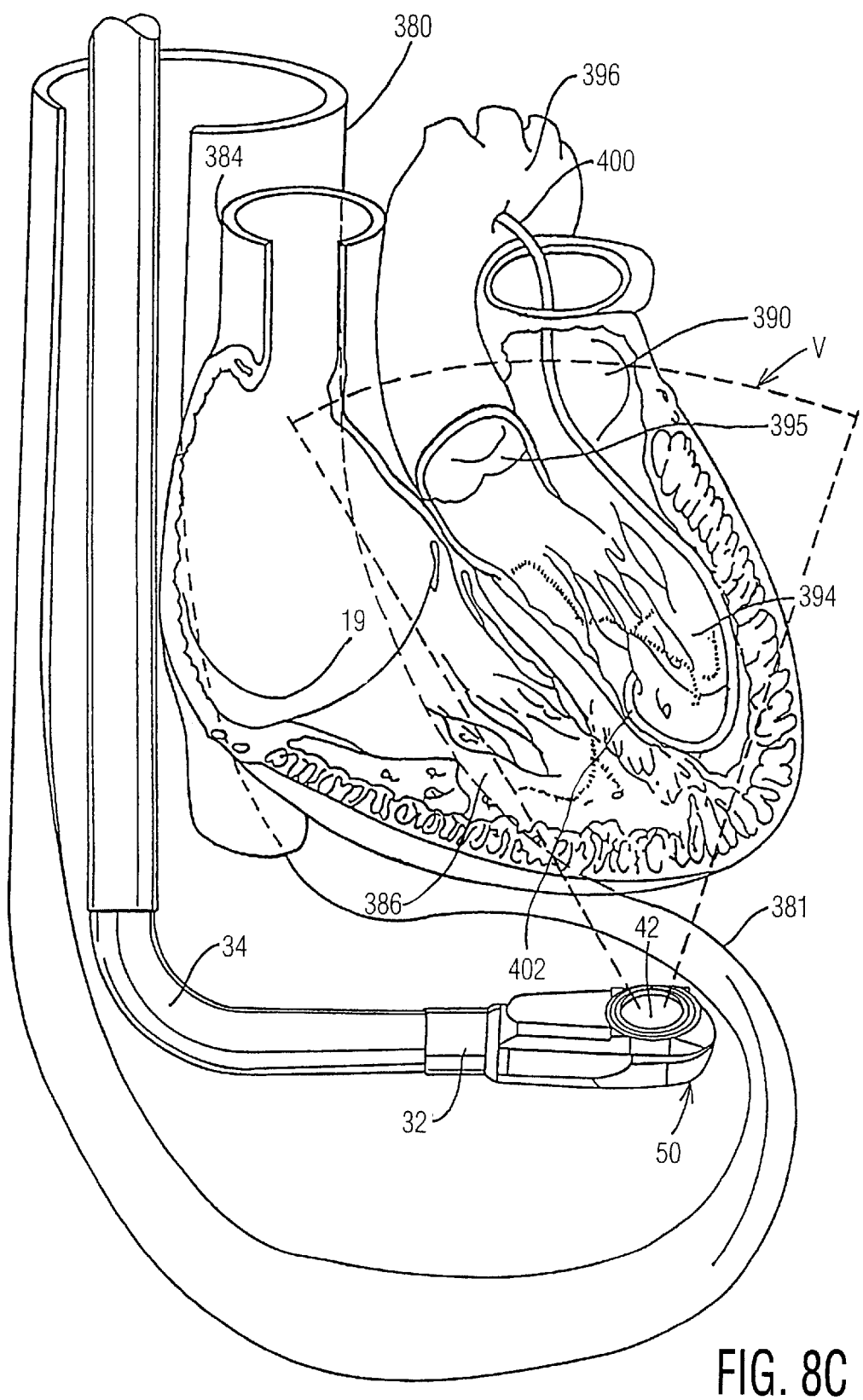

Referring to FIG. 8B, gated peak detector 320 provides the C-scan data that follow a selected tissue surface located within the selected ROI or range. A sampler 352 receives output 319 from post-processor 318 and provides the sampled data to a hold circuit 356 and to a delay circuit 360. Furthermore, the output 329 of majority vote processor 328 is provided to a positive trigger comparator 354 and to a negative trigger comparator 358. When majority vote processor 328 detects the proximal tissue surface, positive trigger comparator 354 provides an enable signal to hold circuit 356, which in turn provides its output 357 to a proximal/distal surface circuit 364.

Proximal/distal surface circuit 364 functions as a switch. When majority vote processor 328 detects the distal surface, negative trigger comparator 358 provides an enable signal to a hold circuit 362, which in turn provides its output 363 to proximal/distal surface switch 364. Proximal/distal surface switch 364 receives a proximal/distal surface value 244 from control processor 200. Depending on the proximal/distal surface output 244, proximal/distal switch provides signal 357 or signal 363 to a yaw adjustment processor 335 and, in turn, to contrast adjustment processor 340. That is, proximal/distal switch 364 determines whether gated peak detector 320 sends the large value from the positive-going edge of the RF signal, or sends the large value from the negative going edge of the RF signal. In this way, the system generates the data for the top view or the bottom view (both being modified C-scan images).

As described above, gated peak detector 320 selects the proximal or distal surface data from the RF signal and sends it to yaw adjustment processor 335. For a zero degree adjustment (i.e., yaw adjustment output 243 equal to zero), the data is provided unchanged to a contrast adjustment processor 340. Contrast adjustment processor 340 achieves a separate contrast adjustment for the bottom view and the top view (i.e., the two C-scan images). A clinician provides a C-scan contrast input 216, which control processor 200 provides as C-scan output 238. For example, a tissue wall may be seen on the front and side views (the B-scan cross-sections) as a white line, but a clinician may want to see it in gray to look for landmarks, lesions or therapy devices in the bottom view. The C-scan contrast creates realistic tissue surface appearance. After the contrast adjustment, contrast adjustment processor 340 provides the contrast adjusted data to a scale adjustment processor 345. Scale adjustment processor 345 maps the contrast adjusted data to the scale used for the front and side views (i.e., B-scan images) and provides the data to video display memory 300.

Also referring to FIG. 9, after viewing the front view (or the rear view) 286 and the side views 291 or 292, a clinician can electronically change or reposition the scan volume V (shown in FIGS. 7 through 7F) by entering new values for scan sector depth 208, frame rate 210, or azimuth-to-elevation scan ratio 212 to perform another scan. The clinician can re-select the imaged tissue by changing a pitch offset 218 or a roll offset 219 of the new scan. The pitch offset changes the scan lines in the azimuthal direction. The roll offset changes the elevation angle of transducer array 42 and thus changes the position of the individual image sectors. This way the clinician can direct a scan over a smaller data volume centered on the tissue of interest. By scanning over the smaller volume, the system improves real-time imaging of moving tissue by increasing the frame rate, because it collects a smaller number of data points. Alternatively, the system collects the same number of data points over the smaller volume to increase the resolution.

An azimuthal icon generator 289 receives a pitch adjustment 241 and provides data for displaying a front azimuthal icon 370 for the front view (or a rear azimuthal icon for the rear view). An elevation icon generator 299 receives a roll adjustment 242 and provides data for displaying a left elevation icon 372 (FIG. 9) for the left view 291 and a right elevation icon 374 for the right view 392. A yaw icon generator receives a yaw adjustment 243 and provides data for displaying a top icon 376 and a bottom icon 425 showing the yaw orientation (FIG. 9). A clinician uses the icons for better understanding of the images. Furthermore, a clinician uses the icon to steer and direct the acoustic beam to a selected value of interest or to locate and orient the images relative to the orientation of transducer array 42.

Figure 10A:
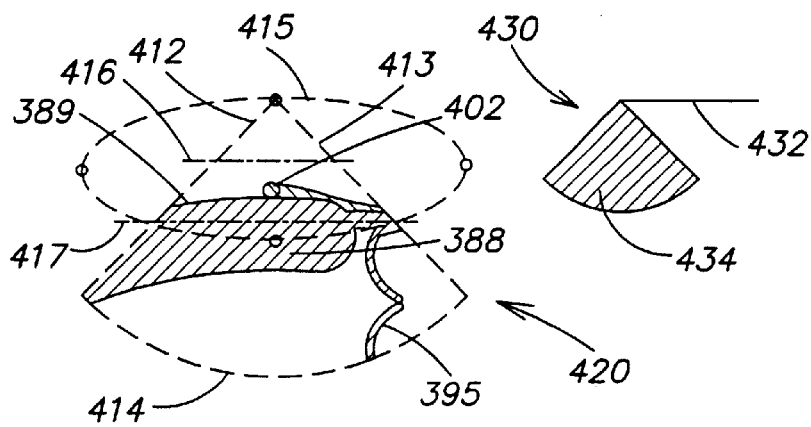
FIG. 10 illustrates the orthographic projection views of FIG. 9 adjusted by changing the yaw angle.
Figure 10B:
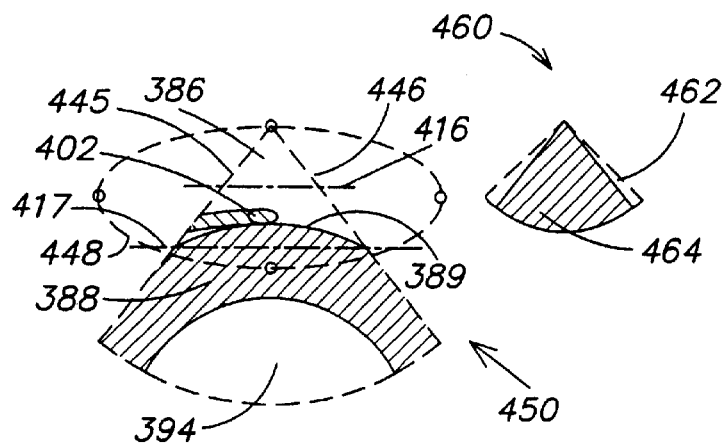
Figure 10C:
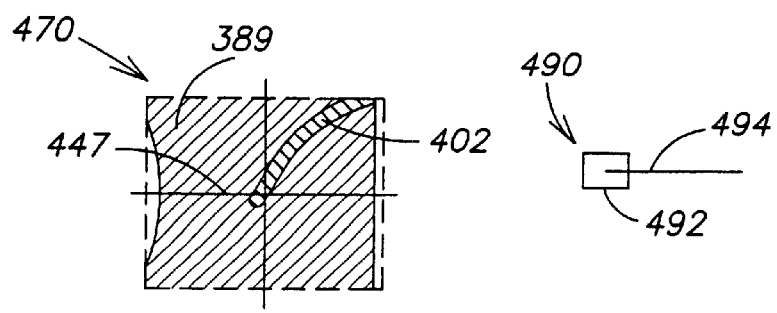
Figure 11B:
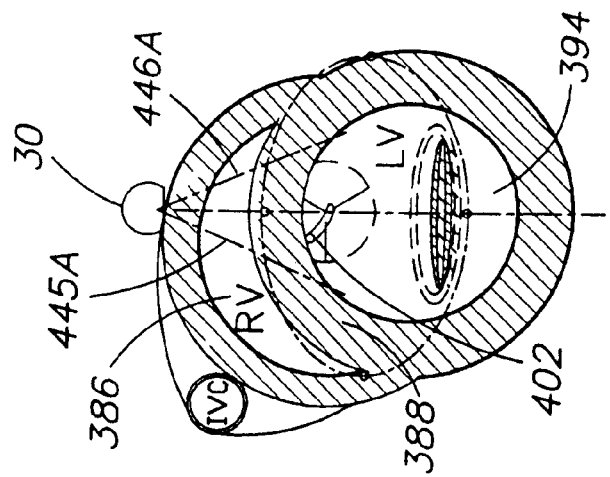
FIG. 11 shows a cross-sectional view of the human heart with the imaging catheter of FIG. 2 positioned in the right atrium.
Figure 11A:
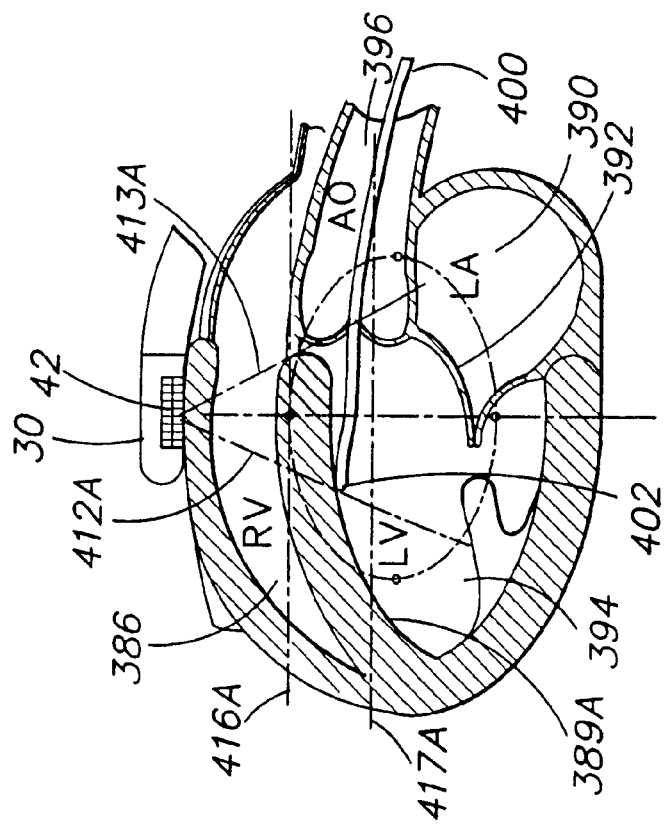
Figure 11C:
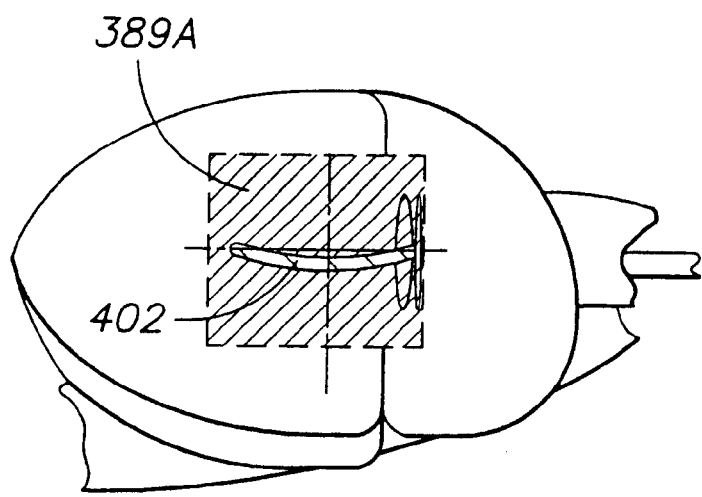
Figure 11D:
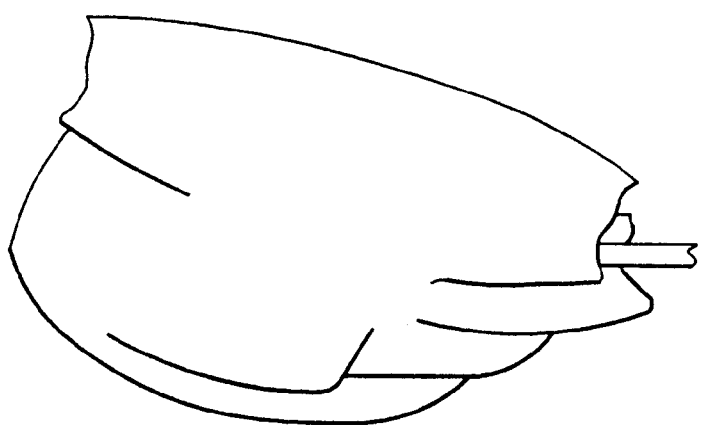

The imaging system can also vary electronically the presentation of the orthographic projection views (i.e., the front, rear, side, top, and bottom views). After viewing the front view and the side views (shown in FIG. 9), a clinician can change the orientation of the views by changing a yaw offset 220. Yaw output 243 is provided to processors 285, 290 and 335, which re-calculate the front, side, top and bottom views. The recalculated front view 286A, left side view 291A, right side view 292A, top view 337A and bottom view 336A are shown in FIG. 10. Furthermore, azimuthal icon generator 289 now provides data for displaying a front azimuthal icon 370A and elevation icon generator 299 provides data for both a left elevation icon 372A and a right elevation icon 374A. The yaw icon generator provides data for displaying both a top icon 376A and a bottom icon 378A.

The yaw adjustment requires interpolation to generate two new planes of scan lines. These are generated from the nearest set of scan lines using the data volume matrix to create the new data planes (i.e., sectors). This interpolation process uses the same principle as the scan conversion process performed by real-time 2D systems that convert the polar coordinate data into the rectangular coordinate data used for the display (see, e.g., U.S. Pat. Nos. 4,468,747 or 5,197,037). Each recalculated data plane can be stored in a memory associated with processors 285 and 290. The re-calculated data planes are provided to video display plane memory 300 and then a video monitor by signal 350 (FIG. 8A). Scan converters 288 and 298 convert the ultrasound data, acquired in R, theta, into an XY format for both the azimuth and elevation planes. Scan converters 288 and 298 are constructed as described in U.S. Pat. Nos. 4,468,747; 4,471,449; or 5,197,037, or "Ultrasound Imaging: an Overview" and "A Scan Conversion Algorithm for Displaying Ultrasound Images", Hewlett-Packard Journal, October 1983.

FIG. 11 shows a cross-sectional view of the human heart with rigid region 32 of ultrasound imaging catheter 12 inserted in the right atrium 380. Catheter 12 can be easily inserted into the vasculature and placed at a desired location. For example, to gain access to the right atrium of the heart, a physician inserts percutaneously the catheter typically through the right or left femoral vein near the groin, or the right jugular vein in the neck (or possibly the subclavian vein in the upper chest). Then, the physician slides the inserted catheter via the inferior vena cava 382 or the superior vena cava 384 into the right atrium.

The imaging system can provide real-time images of the heart cycle as deoxygenated venous blood enters the right atrium 380 of the heart via the inferior vena cava 382 and the superior vena cava 384 and, during diastole, flows to the right ventricle 386. The ventricles are cone-shaped muscular chambers that continuously change their shape. The pulmonary artery (not shown) then delivers blood ejected from the right ventricle into the lungs during systole. The pulmonary vein (not shown) carries oxygenated blood from the lungs to the left atrium 390 of the heart. During diastole, oxygenated blood flows from the left atrium 390 to the left ventricle 394. During systole the left ventricle 394 ejects oxygenated blood into the aorta 396. The imaging system can also collect echo data from tissue of the right or left heart by positioning transducer array 42 in the right atrium 380, which provides an easier access and a somewhat lower risk to the patient.

After positioning transducer array 42 in the right atrium 380, the imaging system can image the left and right heart using the phased array mode or the linear array mode. For example, imaging system 10 can image a medical device, such as a balloon catheter or an ablation catheter, introduced into the heart. An ablation catheter 400 (for example, a catheter manufactured by Medtronics, Inc., Sunnyvale, Calif.) is introduced into the left ventricle 394 having its distal part 402 located near or on an interior surface of the myocardium. A clinician will understand the three-dimensional structure (in time) due to the novel catheter design, described above, and the novel display system that provides anatomically correct orientation of the images. The novel catheter design has the centerline of rotation of transducer array 42 located at the apex of the pie shaped image shown in FIGS. 12A through 17C.

Importantly, the entire system provides six degrees of freedom to acquire and generate high quality images. Imaging catheter 12 provides three degrees of freedom in positioning transducer array 42 relative to the examined tissue. By articulating, rotating and displacing distal part 30, a clinician maneuvers transducer array 42 to a selected position and orients array 42 relative to the examined tissue.

The imaging electronics provides another three degrees of freedom for generating the images by selecting the pitch, roll and yaw values. The display system can generate new (re-oriented) images for different yaw values from the collected scan data stored in the memory. The display format is always predictable from one position (or range of positions) to another and is easily understood by a clinician, as described below.

Figure 12A:
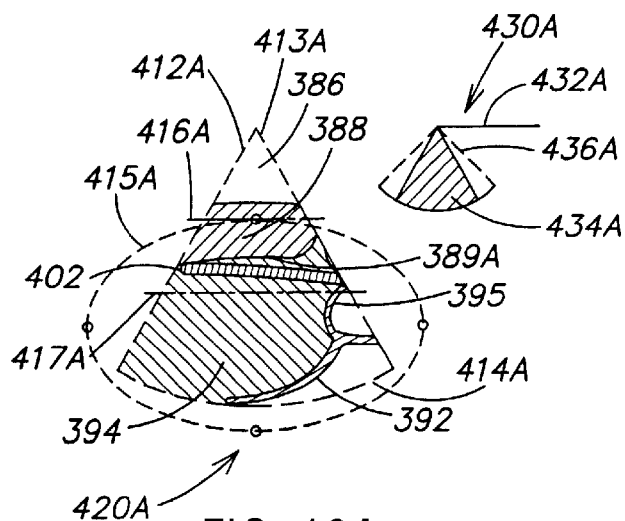
FIGS. 12A and 12B are cross-sectional views of the human heart with the imaging catheter and an ablation catheter positioned in the right ventricle.
Figure 12B:
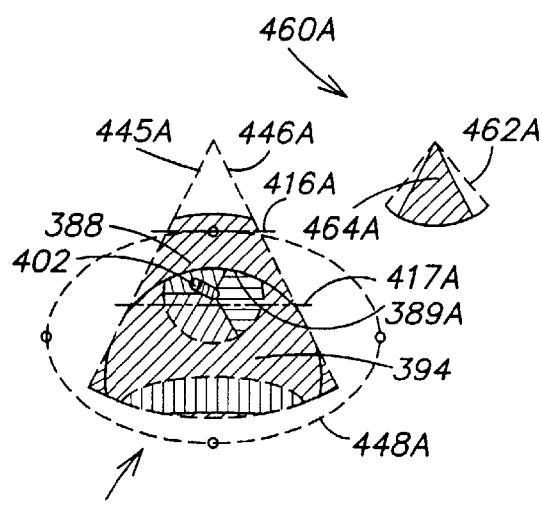

FIG. 12A is a cross-sectional view of the human heart along its long axis, and FIG. 12B is a cross-sectional view along the short axis of the heart. FIGS. 12A through 12D are not displayed on the video display of the imaging system, but are provided here for explanation. Both FIGS. 12A and 12B show distal part 30 of catheter 12 located inside the right ventricle 386 and distal part 402 of ablation catheter 400 also located inside the right ventricle 386. The imaging system uses transducer array 42 to collect the echo data and provides an orthographic front view 420, an orthographic left side view 450, and a top view 470 shown in FIGS. 13A, 13B and 13C, respectively. The video display of the imaging system displays each orthographic projection view and an associated icon, as shown in FIGS. 9 and 10. In the following description, we use the standard definitions of projection views as provided, for example, in *Engineering Drawing and Geometry*, by R. P. Hoelscher and C. H. Springer, John Wiley & Sons, Inc., 1961.

Referring to FIG. 12A, transducer array 42, operating in a phased array mode, collects the echo data over an azimuthal angular range delineated by lines 412 and 413 and a range distance 414. FIG. 13A shows the corresponding front view 420 and a front view icon 430. Front view icon 430 includes an array axis 432 and shows a front view field 434 corresponding to the azimuthal angular range. Array axis 432 shows the longitudinal axis of transducer array 42 for a selected value of yaw adjustment 243 (FIG. 8A). Front view 420 shows distal part 402 of ablation catheter 400 positioned on the proximal surface (top surface) 389 of the septum 388, which separates the right ventricle 386 and the left ventricle 394 (FIG. 12A). Front view 420 also shows the aortic valve 395 between the left ventricle 394 and the aorta 396 (shown in FIG. 12A). A clinician can set the location of gates 416 and 417 and an ROI marker 415.

Figure 13B:
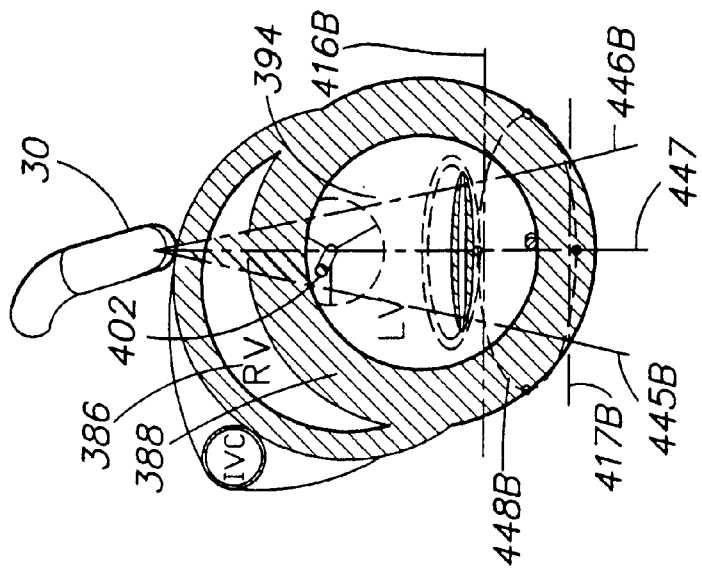
FIGS. 13A, 13B, 13C and 13D are orthographic projection views collected by the imaging catheter shown in FIGS. 12A and 12B.
Figure 13A:
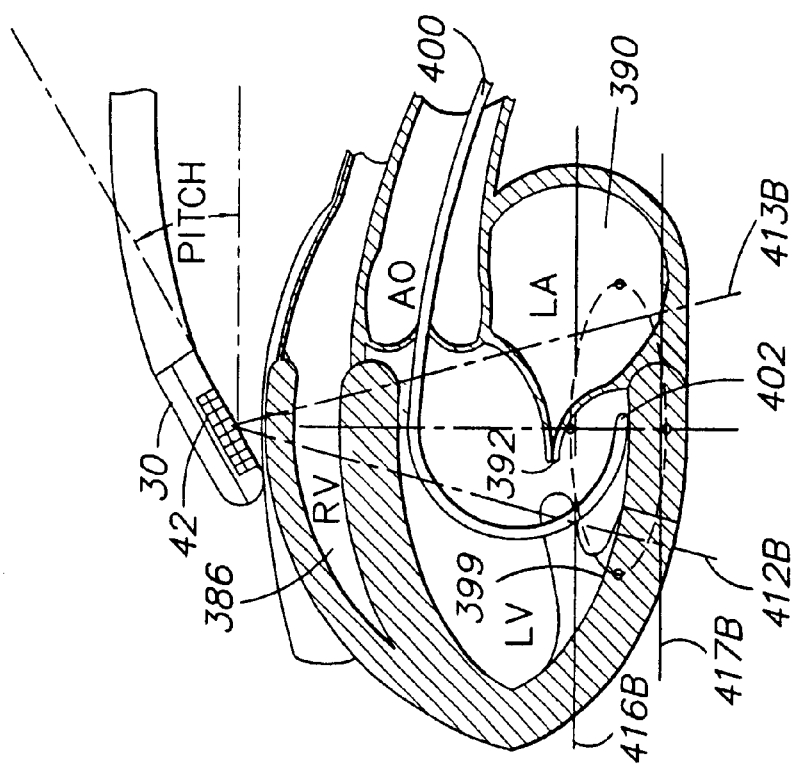

Referring to FIGS. 12B and 13B, the imaging system can also generate a left side view 450 by collecting echo data over a selected elevation angular range delineated by lines 445 and 446 and an ROI marker 448. Transducer array 42 (FIG. 12A) collects echo data over a selected number of image sectors, wherein a line 447 indicates the location of the front view plane. Left side view 450 displays a portion of the left ventricle 394, the right ventricle 386, the septum 388, and distal part 402 of catheter 400, located on the right ventricular surface 389 of the septum 388. Referring still to FIG. 13B, left side view icon 460 shows an available side view field 462 and an actual roll angle 464 over which the image sectors were acquired.

Figure 12C:
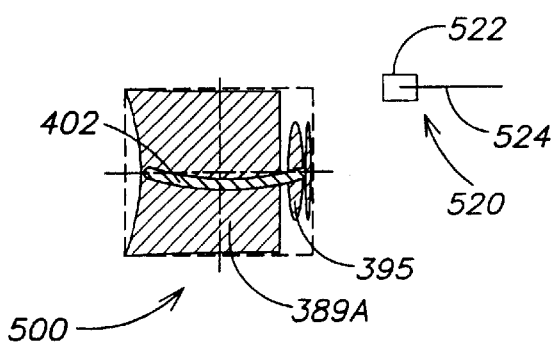
FIG. 12C is a perspective view of the human heart including a cut-away top view displaying the blation catheter shown in FIGS. 12A and 12B.
Figure 13C:
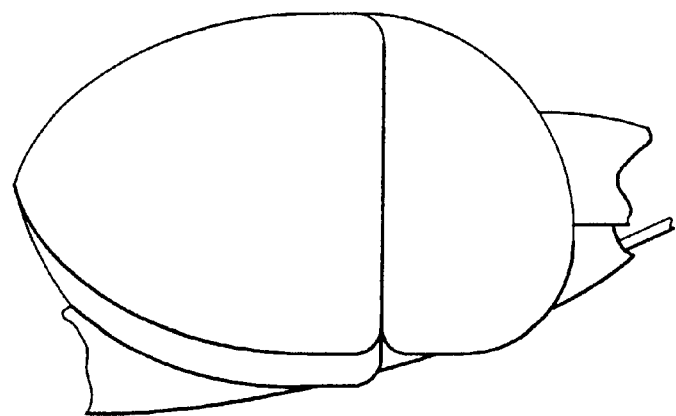
Figure 13D:
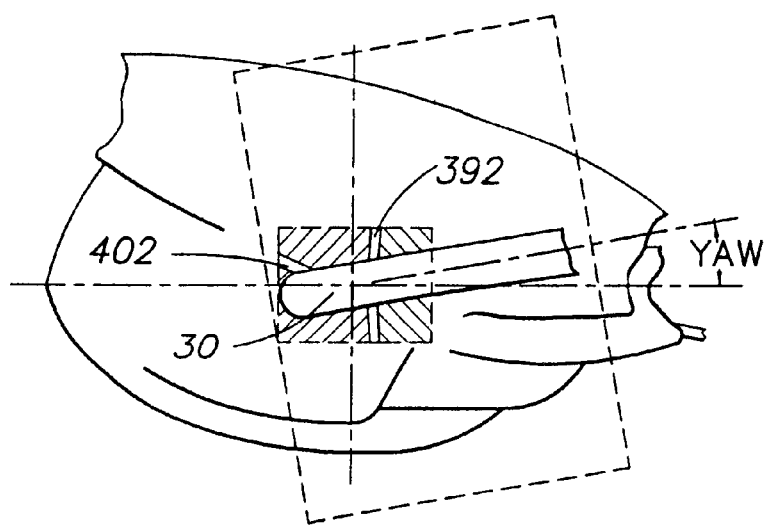

FIGS. 12C and 12D are projection views of the human heart. FIG. 12D shows a cut-away top view displaying distal part 402 of the ablation catheter and the surface of the septum 388 within the ranges (i.e., gates 416 and 417) defined in FIGS. 12A and 12B. The corresponding FIG. 13C displays a C-scan projection, top view 470, generated from the B-scan data within range gates 416 and 417, and displays a top view icon 490. Top view 470 shows distal part 402 of catheter 400 placed on the proximal surface 389 of the septum 388. Range gates 416 and 417 and angular range lines 412, 413, 446, and 448 define the area of top view 470. The area of top view 470 is not identical to the shaded area due to the curvature of the proximal surface 389 of the septum 388. FIG. 13C also displays top view icon 490, which includes a rectangular array 492 and an array axis 494. The angle of axis 494 relative to the side of rectangular area 492 indicates the yaw angle of top view 470, wherein the yaw angle is zero in this case.

Figure 14A:
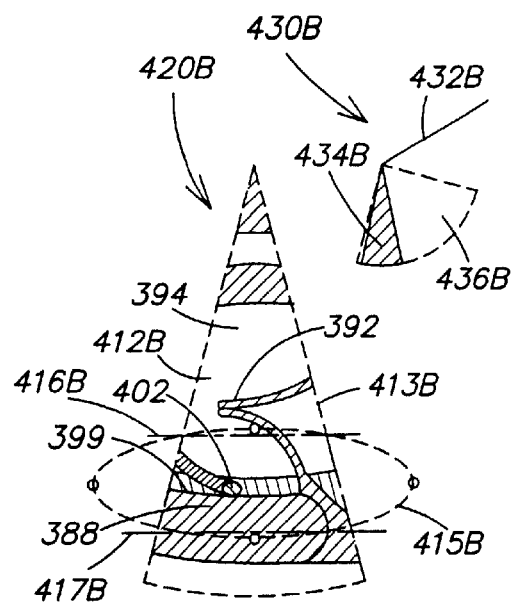
FIGS. 14A and 14B are cross-sectional views of the human heart with the imaging catheter positioned in the right ventricle and an ablation catheter in the left ventricle.
Figure 14B:
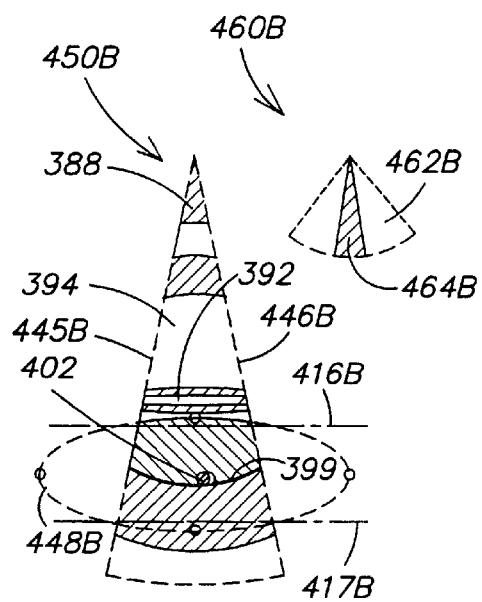

FIGS. 14A and 14B show cross-sectional views of the heart similarly as FIGS. 12A and 12B. The imaging system displays the corresponding front view 420A (shown in FIG. 15A) and a left side view 450A (shown in FIG. 15B). However, in FIGS. 14A and 14B, the imaging system uses different values for range gates 416 and 417 and for angular range lines 412, 413, 446 and 448 than in FIGS. 12A and 12B since distal part 402 of catheter 400 is located now in the left ventricle 394. Furthermore, the imaging system displays a bottom view 500 (shown in FIG. 15C), instead of top view 470, after setting the range gates 416A and 417A in FIGS. 15A and 15B.

FIG. 14A is a cross-sectional view of the heart along the long axis cross-section. The imaging system collects the echo data and generates orthographic front view 420A, shown in FIG. 15A. The system uses a new azimuthal angular range delineated by lines 412A and 413A, which is smaller than the azimuthal angular range used for projection view 420. The smaller azimuthal angular range is selected because the surface of interest is located farther from array 42. In general, in the phased array mode, the imaging system images regions of interest located close to array 42 using larger azimuthal and elevation angular ranges than regions farther away.

Figure 15A:
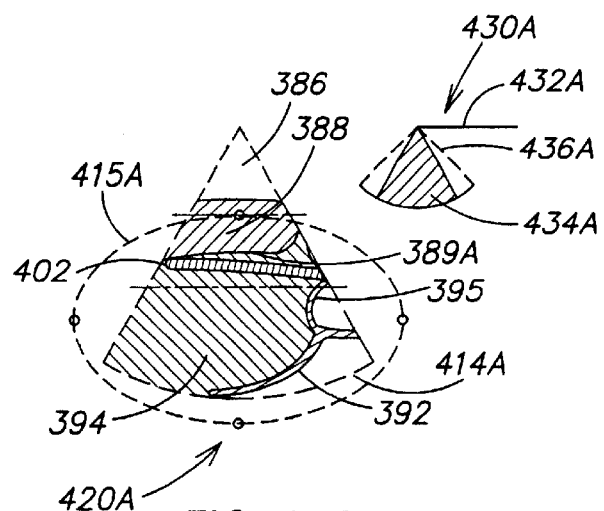
FIGS. 15A, 15B and 15C are orthographic projection views collected by the imaging catheter shown in FIGS. 14A and 14B.

Referring to FIG. 15A, orthographic front view 420A displays the septum 388, distal part 402 of catheter 400, left ventricle 394, and portions of the mitral valve 392 and aortic valve 395, all located within a range 414A. Front view 420A can display distal part 402 of catheter 400 during, for example, ablation or re-vascularization of myocardial tissue. FIG. 15A also displays front view icon 430A that includes array axis 432 located at an angle relative to an actual front view field 434A corresponding to the azimuthal angular range defined by lines 412A and 413A. Front view icon 430A includes an available front view field 436 corresponding to a maximum azimuthal angular range.

FIG. 14B is a cross-sectional view along the short axis of the heart. FIG. 14B shows distal part 30 of catheter 12, located inside the right ventricle 386, and distal part 402 of ablation catheter 400, located inside the left ventricle 394. The imaging system provides orthographic left side view 450A, shown in FIG. 15B.

Figure 15B:
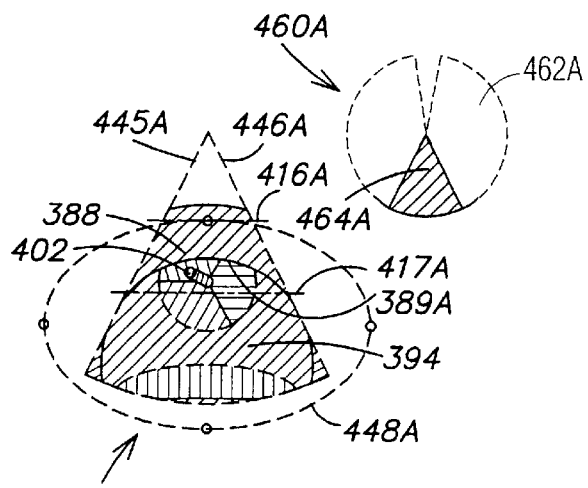

FIG. 15B displays left side view 450A and left side view icon 460A. The imaging system generates left side view 450A, which shows a portion of the left ventricle 394, filled with oxygenated blood, and a portion of the right ventricle 386, filled with de-oxygenated blood. Distal part 402 of catheter 400 is located near the distal surface 389A (bottom surface) of the septum 388 within range gates 416A and 417A. Left side view icon 460A shows an available side view field 462 and an actual side view field 464A. Actual side view field 464A displays the actual angular displacement of transducer array 42, delineated by lines 445A and 446A, over which the image sectors were acquired. Available side view field 462 corresponds to a maximum elevation angular range of transducer array 42.

Figure 14C:
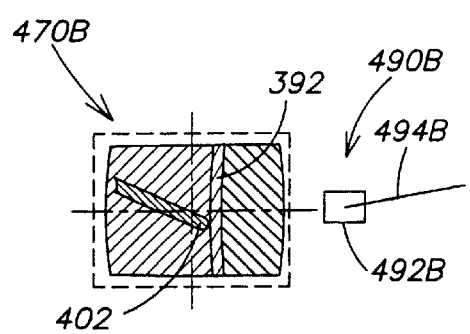
FIG. 14C is a perspective view of the human heart including a cut-away bottom view displaying the ablation catheter shown in FIGS. 14A and 14B.
Figure 15C:
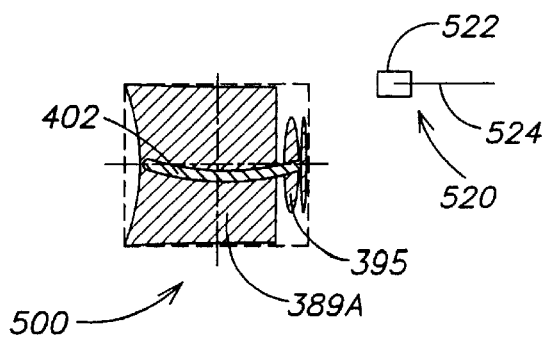

FIGS. 14C and 14D are projection views of the human heart. FIG. 14C shows a cut-away bottom view displaying distal part 402 and bottom surface 389A of the septum 388, both of which are located within the ranges defined in FIGS. 15A and 15B. The corresponding FIG. 15C displays a C-scan projection, bottom view 500, generated from the B-scan data within range gates 416A and 417A. Bottom view 500 shows distal part 402 placed on the distal surface (left ventricular surface) 389A of the septum 388. Range gates 416A and 417A and angular range lines 412A, 413A, 446A, and 445A define the area of bottom view 500. The area of bottom view 500 is not identical to the shaded area due to the curvature of the proximal surface 389A. FIG. 15C also displays bottom view icon 520, which includes a rectangular array 522 and an array axis 524. The angle of axis 524, relative to the side of rectangular area 522 indicates the yaw angle of top view 500. The yaw angle is zero in this case.

The video display of the imaging system displays the above-described orthographic projection images and the associated icons always at the same location, shown in FIG. 9. The conventional location of each image and icon makes it easier for a clinician to correlate the images to the actual anatomy of the imaged tissue. After providing another value of yaw 220 (FIGS. 8 and 8A), the image processor recalculates all orthographic projection views and displays them at the locations shown in FIG. 10. The displayed images thus have anatomically correct orientation.

FIGS. 16A and 16B show cross-sectional views of the heart similar to views shown in FIGS. 14A and 14B, respectively. However, in FIGS. 16A and 16B, the imaging system uses range gates 416B and 417B and for angular range lines 412B, 413B, 446B and 448B since distal part 402 of catheter 400 is located now in the left ventricle 394 on a tissue surface 399. The imaging system displays a top view 470B (shown in FIG. 17C), based on the setting of the range gates in FIGS. 17A and 17B.

FIGS. 16A and 16B show distal part 30 of catheter 12 located inside the right ventricle 386 and a distal part 402 of ablation catheter 400 also located inside the left ventricle 394. As described above, the imaging system uses transducer array 42 to collect the echo data and generate orthographic projection views shown in FIGS. 17A, 17B and 17C. The video display displays the orthographic projection views and the associated icon on the predetermined locations shown in FIGS. 9 and 10.

Specifically, FIG. 17A shows the corresponding cross-sectional view 420B and a front view icon 430B. Front view 420B shows distal catheter part 402 positioned on tissue surface 399. Front view 420B also shows the mitral valve 392 between the left ventricle 394 and the left atrium 390. A clinician can set the location of gates 416B and 417B and an ROI marker 415B. Front view icon 430B displays an array axis 432B and displays an available front view field 436B and an actual front view field 434B. Actual front view field 434B corresponds to the azimuthal angular range defined by lines 412B and 413B, and available front view field 436B corresponds to a maximum azimuthal angular range. The relationship between actual view field 434B and available view field 436B displays pitch adjustment 241 (FIG. 8). Array axis 432B relative to actual view field 436B shows a selected value of yaw adjustment 243 (FIG. 8).

Referring to FIGS. 16B and 17B, the imaging system can also generate a left side view 450B by collecting echo data over a selected elevation angular range delineated by lines 445B and 446B and an ROI marker 448B. Left side view 450B displays a portion of septum 388, interior of the left ventricle 394, a portion of the mitral valve 392 and distal catheter part 402, located on the left ventricular surface 399. Referring still to FIG. 17B, left side view icon 460B displays an available side view field 462B and an actual side view field 464B, which corresponds to roll angle over which the image sectors were acquired. The relationship between available view field 462B and actual view field 464B displays roll adjustment 242 (FIG. 8).

FIGS. 16C and 16D are projection views of the human heart. FIG. 16D shows a cut-away top view displaying both distal part 30 of catheter 12 and distal part 402 of ablation catheter 400 located on the cardiac. FIG. 17C displays a C-scan projection, top view 470B, generated from the B-scan data within range gates 416B and 417B, and displays a top view icon 490B. Top view 470B shows distal catheter part 402, located near surface 399, and a portion of the mitral valve 392. Range gates 416B and 417B and angular range lines 412B, 413B, 446B, and 448B define the area of top view 470B. FIG. 17C also displays top view icon 490B, which includes a rectangular array 492B and an array axis 494B. The angle of axis 494B relative to the side of rectangular area 492B indicates the yaw angle of top view 470B.

When the imaging system images tissue located very close to the transducer array, the system can switch from the phase array scanning mode to the linear scanning mode and provide again the three orthographic projection images described above.

What is claimed is:

1. In an ultrasound system for imaging biological tissue, including an array of ultrasound transducers connected to a transmit beamformer and a receive beamformer constructed to acquire an ultrasound image of a selected tissue region, an intravascular catheter comprising:

a steerable guide sheath including a distal sheath part and a proximal sheath part constructed for insertion into a blood vessel, said distal sheath part including an articulation region constructed to assume a selected orientation;

an imaging core including a distal core part, located within said distal sheath part, and a proximal core part located within said proximal sheath part and being constructed for rotational motion inside said guide sheath, said imaging core including said ultrasound transducer array disposed longitudinally on said distal core part;

a positioning device constructed to control said selected orientation of said articulation region and thereby orient said ultrasound transducer array relative to the tissue region;

said ultrasound transducer array constructed to detect ultrasound data over an image sector defined by an azimuthal angular range; and a rotation device constructed to rotationally displace, over an elevation angular range, said ultrasound transducer array about the apex of said image sector.

2. The intravascular catheter of claim 1 further constructed and arranged for real-time imaging capable of achieving scanning frequencies of about 15 Hz.

3. The intravascular catheter of claim 1 wherein said rotation device is disposed within a catheter handle that further includes a compensation mechanism arranged to counter balance the motion of said rotation device to reduce unwanted vibrations of said handle.

4. The intravascular catheter of claim 3 wherein said rotation device includes a drive motor connected to said imaging core and said compensation mechanism includes a counter balance motor.

5. The intravascular catheter of claim 4 wherein said compensation mechanism is designed to have a natural frequency response at a frequency of oscillation of said ultrasound array.

6. The intravascular catheter of claim 1 wherein said rotation device includes a drive motor constructed and arranged to oscillate said ultrasound array over several different angles of said angular displacement.

7. The intravascular catheter of claim 1 wherein said rotation device is further constructed and arranged to position said ultrasound array at a selected angle relative to said selected tissue region and maintain said array at said angle for a selected period of time.

8. The intravascular catheter of claim 1 further comprising a set of bearings disposed between said imaging core and said guide sheath and arranged to facilitate said oscillation of said ultrasound array about the apex of said image sector.

9. The intravascular catheter of claim 3 wherein said catheter handle includes an accelerometer connected to said compensation mechanism and arranged to detect said unwanted vibrations of said handle.

10. The intravascular catheter of claim 1 further comprising a position sensor constructed and arranged to detect orientation of said ultrasound array relative to a reference orientation and provide a feedback to said rotation device.

11. The intravascular catheter of claim 1 further comprising an accelerometer sensor arranged to detect vibrations caused by said rotation device.

12. The intravascular catheter of claim 1 wherein said articulation region includes a multiplicity of links cooperatively arranged with a push-pull rod connected said positioning device.

13. The intravascular catheter of claim 12 further comprising a sensor instructed and arranged to detect displacement of said push-pull rod.

14. The intravascular catheter of claim 12 wherein said push-pull rod is connected to a rack and pinion mechanism at its proximal end.

15. The intravascular catheter of claim 12 wherein said links and said push-pull rod are cooperatively arranged to flex in-plane said distal portion upon actuation by said positioning device.

16. The intravascular catheter of claim 15 further comprising a second push-pull rod cooperatively arranged with said links to flex out-of-plane said distal portion upon actuation by said positioning device.

17. The intravascular catheter of claim 1 further comprising two push-pull rods and a multiplicity of links included in said articulation region, said multiplicity of links being cooperatively arranged with said push-pull rods to flex in-plane said distal portion to form an S-like curve upon actuation of said push-pull rods by said positioning device.

18. The intravascular catheter of claim 17 further comprising a third push-pull rod cooperatively arranged with said links to further flex out-of-plane said distal portion upon actuation by said positioning device.

19. The intravascular catheter of claim 1 wherein said imaging core includes a drive shaft constructed to exhibit a high torsional stiffness and a high bending flexibility.

20. The intravascular catheter of claim 19 wherein said drive shaft is made of at least two counter wound springs.

21. The intravascular catheter of claim 1 wherein said imaging core is removably insertable into said steerable guide sheath.

22. The intravascular catheter of claim 21 further including a sheath handle connected to said steerable guide sheath and removably connectable to said catheter handle.

23. The intravascular catheter of claim 7 further comprising a position sensor constructed and arranged to provide feedback about a position of said imaging core to said drive motor.

24. The intravascular catheter of claim 23 wherein said drive motor includes a rotary encoder constructed and arranged to provide a angular position feedback to said rotation device.

25. An ultrasound system for imaging biological tissue comprising:
   a catheter with a catheter handle and an elongated body for insertion into a blood vessel, said catheter including
      core means including an ultrasound transducer array disposed longitudinally on a distal part of said core means,
      guide sheath means for receiving said core means and enabling defined rotational movement of said core means,
      articulation means connected to positioning means for orienting said transducer array relative to tissue of interest, and
      rotation means, connected to said core means, for oscillating said transducer array over a selected elevation angular range;
   a transmit beamformer and a receive beamformer connected to said transducer array and constructed to acquire, for each elevation angle of said transducer array, ultrasound data of an image sector defined by an azimuthal angular range; and
   an image generator constructed to receive ultrasound data over a multiplicity of image sectors for different elevation angles within said elevation angular range, said image generator being arranged to form an image of said tissue of interest from said ultrasound data.

26. The ultrasound system of claim 25 wherein said core means and said guide sheath means are arranged so that said transducer array rotates about the apex of said image sector.

27. The ultrasound system of claim 25 further comprising vibration control means located inside said catheter handle and cooperatively arranged with said rotation means to limit vibrations caused by said rotation means.

28. The ultrasound system of claim 25 further comprising means for performing a four dimensional scan of said tissue of interest.

29. The ultrasound system of claim 25 wherein said articulation means are constructed to orient said transducer array by displacing a distal part of said elongated body as an in-plane J hook.

30. The ultrasound system of claim 25 wherein said articulation means are constructed to orient said transducer array by displacing a distal part of said elongated body as an out-of-plane J hook.

31. The ultrasound system of claim 25 wherein said articulation means are constructed to orient said transducer array by displacing a distal part of said elongated body as an S hook.

* * * * *